United States Patent
Duffield et al.

(10) Patent No.: US 9,970,011 B2
(45) Date of Patent: *May 15, 2018

(54) METHODS FOR TREATMENT OF ALPORT SYNDROME

(71) Applicant: Regulus Therapeutics Inc., San Diego, CA (US)

(72) Inventors: Jeremy Duffield, Seattle, WA (US); Balkrishen Bhat, Cambridge, MA (US); Deidre MacKenna, San Diego, CA (US)

(73) Assignee: Regulus Therapeutics Inc., San Diego, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/606,554

(22) Filed: May 26, 2017

(65) Prior Publication Data

US 2017/0369879 A1    Dec. 28, 2017

Related U.S. Application Data

(63) Continuation of application No. 15/151,290, filed on May 10, 2016, now Pat. No. 9,688,986, which is a continuation of application No. 14/677,387, filed on Apr. 2, 2015, now Pat. No. 9,359,609, which is a continuation of application No. 14/048,827, filed on Oct. 8, 2013, now Pat. No. 9,012,423.

(60) Provisional application No. 61/779,137, filed on Mar. 13, 2013, provisional application No. 61/711,514, filed on Oct. 9, 2012.

(51) Int. Cl.
| | |
|---|---|
| *C07H 21/02* | (2006.01) |
| *C07H 21/04* | (2006.01) |
| *A61K 31/70* | (2006.01) |
| *C12N 15/113* | (2010.01) |
| *A61K 45/06* | (2006.01) |
| *A61K 31/7088* | (2006.01) |

(52) U.S. Cl.
CPC ........ *C12N 15/113* (2013.01); *A61K 31/7088* (2013.01); *A61K 45/06* (2013.01); *C12N 2310/113* (2013.01); *C12N 2310/313* (2013.01); *C12N 2310/315* (2013.01); *C12N 2310/321* (2013.01); *C12N 2310/3233* (2013.01)

(58) Field of Classification Search
None
See application file for complete search history.

(56) References Cited

U.S. PATENT DOCUMENTS

| | | | |
|---|---|---|---|
| 7,582,744 B2 | 9/2009 | Manoharan et al. | |
| 8,017,763 B2 | 9/2011 | Manoharan et al. | |
| 8,110,558 B2 | 2/2012 | Bennett et al. | |
| 8,211,867 B2 | 7/2012 | Bennett et al. | |
| 8,236,777 B2 | 8/2012 | Thum et al. | |
| 8,404,659 B2 | 3/2013 | Kauppinen et al. | |
| 8,466,120 B2 | 6/2013 | Lollo et al. | |
| 8,592,389 B2 | 11/2013 | Thum et al. | |
| 8,697,663 B2 | 4/2014 | Bennett et al. | |
| 8,912,161 B2 | 12/2014 | Bhat | |
| 8,969,317 B2 | 3/2015 | Bhat et al. | |
| 9,012,423 B2 | 4/2015 | Duffield et al. | |
| 9,181,547 B2 | 11/2015 | Bhat | |
| 9,267,137 B2 | 2/2016 | Bhat et al. | |
| 9,359,609 B2 | 6/2016 | Duffield et al. | |
| 2009/0192102 A1 | 7/2009 | Bader et al. | |
| 2009/0326208 A1 | 12/2009 | Carrino et al. | |
| 2013/0289093 A1 | 10/2013 | Bhat et al. | |
| 2014/0100263 A1 | 4/2014 | Duffield et al. | |
| 2014/0107183 A1 | 4/2014 | Bhat | |
| 2014/0329887 A1 | 11/2014 | Bhat | |
| 2015/0218558 A1 | 8/2015 | Bhat et al. | |
| 2015/0299704 A1 | 10/2015 | Duffield et al. | |
| 2016/0138016 A1 | 5/2016 | Bhat | |
| 2016/0244753 A1 | 8/2016 | Bhat et al. | |
| 2016/0319283 A1 | 11/2016 | Duffield et al. | |

FOREIGN PATENT DOCUMENTS

| | | |
|---|---|---|
| EP | 2261333 A2 | 12/2010 |
| WO | 9961040 | 12/1999 |
| WO | 2003029459 A2 | 4/2003 |
| WO | 2005013901 A2 | 2/2005 |
| WO | 2006019659 A1 | 2/2006 |
| WO | 2006029173 A2 | 3/2006 |
| WO | 2006069584 A2 | 7/2006 |
| WO | 2006118806 A1 | 11/2006 |

(Continued)

OTHER PUBLICATIONS

Krutzfeldt et al., "Specificity, duplex degradation and subcellular localization of antagomirs," Nucleic Acid Res., 2007, 35(9):2885-2892.

Liu et al., "miR-21 mediates fibrogenic activation of pulmonary fibroblasts and lung fibrosis," J Exp Med., 2010, 207:1589-1597.

MacKenna et al., "Inhibition of miR-21 as an anti-fibrotic agent in Chronic Kidney Disease," Poster, Keystone Symposium, Mar. 30-Apr. 4, 2012, 1 page.

(Continued)

*Primary Examiner* — Sean McGarry
(74) *Attorney, Agent, or Firm* — McNeill Baur PLLC

(57) ABSTRACT

Provided herein are methods for the treatment of Alport Syndrome, using modified oligonucleotides targeted to miR-21. In certain embodiments, a modified oligonucleotide targeted to miR-21 improves kidney function and/or reduces fibrosis in subjects having Alport Syndrome. In certain embodiments, administration of a modified oligonucleotide targeted to miR-21 delays the onset of end-stage renal disease in a subject having Alport Syndrome. In certain embodiments, a modified oligonucleotide targeted to miR-21 delays the need for dialysis or kidney transplant in a subject having Alport Syndrome.

11 Claims, 9 Drawing Sheets

(56) References Cited

FOREIGN PATENT DOCUMENTS

| WO | 2006137941 A2 | 12/2006 |
|---|---|---|
| WO | 2007027894 A2 | 3/2007 |
| WO | 2007090073 A2 | 8/2007 |
| WO | 2007112753 A2 | 10/2007 |
| WO | 2007112754 A2 | 10/2007 |
| WO | 2008043521 A2 | 4/2008 |
| WO | 2008086807 A2 | 7/2008 |
| WO | 2008151631 A2 | 12/2008 |
| WO | 2009043353 A2 | 4/2009 |
| WO | 2009058907 A2 | 5/2009 |
| WO | 2009091972 A2 | 7/2009 |
| WO | 2009099326 A1 | 8/2009 |
| WO | 2009106367 A1 | 9/2009 |
| WO | 2009106477 A1 | 9/2009 |
| WO | 2010099161 A1 | 9/2010 |
| WO | 2010144485 A1 | 12/2010 |
| WO | 2011126842 A2 | 10/2011 |
| WO | 2012148952 A1 | 11/2012 |
| WO | 2013013165 A2 | 1/2013 |
| WO | 2013163258 A1 | 10/2013 |
| WO | 2013192576 A2 | 12/2013 |
| WO | 2014048441 A1 | 4/2014 |
| WO | 2014058881 A1 | 4/2014 |

OTHER PUBLICATIONS

MacKenna et al., "Inhibition of microRNA-21 as a Therapeutic Strategy for Kidney Fibrosis," Kidney Week Nov. 12, 2011, 13 pages.

MacKenna et al., "Inhibition of microRNA-21 as Therapeutic Strategy for Kidney Fibrosis," Abstract SA-OR449, Kidney Week 2011, 1 page.

MacKenna et al., "Inhibition of miR-21 with RG-012 improves renal function and survival in multiple strains of Col4A3 deficient mice," Poster, 10th Annual Meeting of the Oligonucleotide Therapeutics Society, Oct. 12-15, 2014, 1 page.

MacKenna, "microRNA control of human disease: Utility of miR-21 as an anti-fibrotic approach in kidney," Experimental Biology Apr. 22, 2012 Presentation, 20 pages.

MacKenna, "microRNA Therapeutics to Treat Alport Syndrome," Presentation, 2nd Orphan Drugs Research & Commercialization Conference, Feb. 21, 2014, 15 pages.

Meng et al., MicroRNA-21 Regulates Expression of the PTEN Tumor Suppressor Gene in Human Hepatocellular Cancer, Gastroenterology, 2007, 133:647-658.

Milam et al., " PPAR-γ agonists inhibit profibrotic phenotypes in human lung fibroblasts and bleomycin-induced pulmonary fibrosis," Am J Physiol Lung Cell Mol Physiol, 2008, 294:L891-L901.

Noone et al., "An update on the pathomechanisms and future therapies of Alport syndrome," Pediatr Nephrol, 2012, 28: 1025-1036.

Patrick et al., "Response to Thum et al.," J Clin Invest, 2011, 121(2):462-463.

Patrick et al., "Stress-dependent cardiac remodeling occurs in the absence of microRNA-21 in mice," J Clin Invest, 2010, 120(11):3912-3916.

Regulus Press Release, Regulus to Present New RG-012 Data at The 53rd European Renal Association-European Dialysis and Transplant Association (ERA-EDTA) Congress, May 20, 2016, 3 pages.

Regulus Therapeutics, "Regulus Presents New Preclinical Data on miR-21 at Kidney Week 2012," Press Release, Regulus Therapeutics, Nov. 3, 2012, 2 pages.

Regulus Therapeutics, "Regulus Presents Positive Preclinical Data Demonstrating that microRNA-21 Plays an Important Role in Alport Syndrome," Press Release, Regulus Therapeutics, Nov. 8, 2013, 2 pages.

Regulus Therapeutics, "Regulus Therapeutics to Present New In Vivo Data for microRNA-21 in Kidney Fibrosis," Press Release, Regulus Therapeutics, Nov. 8, 2011, 2 pages.

Regulus Therapeutics, "Regulus and Sanofi Present New Data Enhancing the Preclinical Profile of RG-012, an Anti-miR Targeting microRNA-21 for the Treatment of Renal Dysfunction in Alport Syndrome Patients, at ASN's Kidney Week 2014 Meeting," Press Release, Regulus Therapeutics, Nov. 15, 2014, 3 pages.

Regulus Therapeutics, "Regulus Initiates Phase I Clinical Study of RG-012, a microRNA Therapeutic in Development for the Treatment of Alport Syndrome," Press Release, Regulus Therapeutics, Jun. 4, 2015, 3 pages.

Regulus Therapeutics, "Regulus to Present Additional Preclinical Data Supporting RG-012 as a Novel microRNA Therapeutic in Development for Alport Syndrome at ASN's Kidney Week 2015," Press Release, Regulus Therapeutics, Oct. 5, 2015, 3 pages.

Rheault et al., ERA-EDTA 2016 Congress, Abstract SP120, Change in Glomerular Filtration Rate and Renal Biomarkers in Patients with Chronic Kidney Disease Due to Alport Syndrome: Interim Results from the ATHENA Study, a Prospectively Designed Natural History Study, May 2016, 1 page.

Rheault et al., ERA-EDTA 2016 Congress, Poster SP120, Change in Glomerular Filtration Rate and Renal Biomarkers in Patients with Chronic Kidney Disease Due to Alport Syndrome: Interim Results from the ATHENA Study, a Prospectively Designed Natural History Study, May 2016, 1 page.

Rheault et al., Kidney Week 2016, Abstract PUB183, Predictors of Rapid Progression in Women with X-linked Alport Syndrome, Oct. 2016, 1 page.

Rubel et al., "Anti-microRNA21 therapy on top of ACE-inhibition enhances nephroprotection," Poster, American Society of Nephrology Kidney Week, Nov. 11-16, 2014, 1 page.

Saal et al., "MicroRNAs and the kidney: coming of age," Curr Opin Nephrol Hy, 2009, 18: 317-323.

Seth et al., "Design, Synthesis and Evaluation of Constrained Methoxyethyl (cMOE) and Constrained Ethyl (cEt) Nucleoside Analogs," Nucleic Acids Symposium Series, 2008, 52:553-554.

Szeto et al., "Micro-RNA Expression in the Urinary Sediment of Patients with Chronic Kidney Diseases," Dis Markers, 2012, 33: 137-144.

Thum et al., "Comparison of different miR-21 inhibitor chemistries in a cardiac disease model," J Clin Invest, 2011, 121:461-462.

Thum et al., "MicroRNA-21 contributes to myocardial disease by stimulating MAP kinase signalling in fibroblasts," Nature, 2008, 456:980-986.

Wynn, "Common and unique mechanisms regulate fibrosis in various fibroproliferative diseases," J Clin Invest., 2007, 117:524-529.

Zarjou et al, "Identification of microRNA signature in renal fibrosis: role of miR-21," Am J Physiol Renal Physiol, 2011, 301:F793-F801.

Zhong et al., "Smad3-Mediated Upregulation of miR-21 Promotes Renal Fibrosis," J Am Soc Nephrol, 2011, Including supplemental data 22:1668-1681.

Akkina et al., "MicroRNAs in kidney function and disease," Transl Res, Elsevier, Amsterdam, NL, 2011, 157: 236-240.

Androsavich et al., "Novel Methodology for Assessing Inhibition of MicroRNA-21 by RG-012, a MicroRNA Therapeutic in Development for the Treatment of Kidney Dysfunction in Patients with Alport Syndrome," Abstract SA-PO539, Kidney Week 2015, Oct. 2015, 1 page.

Androsavich et al., "Novel Methodology for Assessing Inhibition of MicroRNA-21 by RG-012, a MicroRNA Therapeutic in Development for the Treatment of Kidney Dysfunction in Patients with Alport Syndrome," Kidney Week 2015 Poster, Nov. 7, 2015, 1 page.

Blem et al., "A Natural History Study to Observe Disease Progression, Standard of Care, and Investigate Biomarkers in Alport Syndrome Patients," Abstract PUB119, Kidney Week 2015, Oct. 2015, 1 page.

Boulanger et al., "Anti-miR-21 as a Potential Novel Therapy for both Early and Late Stages of Alport Syndrome," Kidney Week Presentation, Nov. 15, 2014, 12 pages.

Boulanger et al., "Identification of the Pathologic Role of miR-21 in Alport's Kidney Disease," Abstract No. FR-P0697, Kidney Week, Oct. 16, 2013, 1 page.

(56) References Cited

OTHER PUBLICATIONS

Boulanger et al., "Identification of the Pathologic Role of miR-21 in Alport's Kidney Disease," Kidney Week 2013 Poster, Nov. 8, 2013, 1 page.
Carroll et al., "Potent and Selective Antisense Oligonucleotides Targeting Single-Nucleotide Polymorphisms in the Huntington Disease Gene / Allele-Specific Silencing of Mutant Huntingtin," Molecular Therapy, 2011, 19(12): 2178-2185.
Chan et al., "MicroRNA-21 Is an Antiapoptotic Factor in Human Glioblastoma Cells," Cancer Res., 2005, 65:6029-6033.
Chau et al., "MicroRNA-21 Promotes Fibrosis of the Kidney by Silencing Metabolic Pathways," Sci Transl Med., 2012, 4:121ra18.
Chau, "microRNAs—Novel Therapeutic Targets for Kidney Diseases," ASN Kidney Week 2011, Philadelphia, PA, Presentation, Nov. 8, 2011, 24 pages.
Chen et al., "Relation between MicroRNA Expression in Peritoneal Dialysis Effluent and Peritoneal Transport Characteristics," Dis Markers, 2012, 33:35-42.
Cosgrove, "Glomerular pathology in Alport syndrome: a molecular perspective," Pediatr Nephrol, 2011, 27:885-890.
Davis et al., "Improved targeting of miRNA with antisense oligonucleotides," Nucleic Acids Res., 2006, 34:2294-2304.
Duffield et al., "Inhibition of microRNA-21 as a Therapeutic Strategy for Kidney Fibrosis," Abstract SA-OR449, Kidney Week Oct. 3, 2011, 1 page.
Duffield, "MicroRNAs are Novel Therapeutic Targets to Treat Kidney Injury and Fibrosis," Presentation, Kidney Week, Atlanta, GA, Nov. 5-10, 2013, 31pages.
Duffield, "Mitochondiral Dysfunction in the Progression of Chronic Kidney Disease," Renal Grand Rounds, Seattle, WA, Sep. 20, 2013, 44 pages.
Esau, "Inhibition of microRNA with antisense oligonucleotides," Methods, 2008, 44:55-60.
File history for U.S. Appl. No. 14/111,976, filed Apr. 25, 2012.
File history for U.S. Appl. No. 14/444,406, filed Jul. 28, 2014.
File history for U.S. Appl. No. 14/597,676, filed Jan. 15, 2015.
File history for U.S. Appl. No. 15/441,590, filed Feb. 24, 2017.
File history of U.S. Appl. No. 13/869,177, filed Apr. 24, 2013.
File history of U.S. Appl. No. 14/048,827, filed Oct. 8, 2013.
File history of U.S. Appl. No. 14/677,387, filed Apr. 2, 2015.
File history of U.S. Appl. No. 14/883,055, filed Oct. 14, 2015.
File history of U.S. Appl. No. 14/995,432, filed Jan. 14, 2016.
File history of U.S. Appl. No. 15/151,290, filed May 10, 2016.
Godwin et al., "Identification of a microRNA signature of renal ischemia reperfusion injury," PNAS, 2010, 107:14339-14444.
Gomez et al., "Anti-microRNA-21 oligonucleotides prevent Alport nephropathy progression by stimulating metabolic pathways," J Clin Invest., 2015, 125:141-156, includes Supplemental Data.
Gomez et al., "Anti-micro-RNA-21 rescues kidney function in Alport Nephropathy," Kidney Week 2013 Presentation, Nov. 9, 2013, 16 pages.
Gomez et al., "Anti-miR21 Protects Collagen 4A3 Deficient Mice from Progression of Alport Disease by Decreasing Oxidative Stress," Abstract SA-OR094, Kidney Week Oct. 16, 2013, 1 page.
Gomez et al., "Anti-miR21 Protects Collagen 4A3 Deficient Mice from Progression of Alport Disease," Abstract SA-PO1134, Kidney Week Oct. 10, 2012, 1 page.
Gomez et al., "Anti-miR21 Protects Collagen IVa(3) Deficient Mice from Progression of Alport Disease," Poster, Keystone Symposium, Mar. 23-28, 2014, 1 Page.
Gomez et al., "Anti-miR21 Protects Collagen IV-alpha(3) Deficient Mice from Progression of Alport Disease," Kidney Week 2012 Poster, Nov. 3, 2012, 1 page.
Gross et al., "Treatment of Alport syndrome: beyond animal models," Kidney Int, 2009, 76:599-603.
Gross et al., Kidney Week 2016, Abstract FR-PO636, Progression of Chronic Kidney Disease in Alport Syndrome: Interim Data from the ATHENA Study, Oct. 2016, 1 page.
Gross et al., Kidney Week 2016, Poster FR-PO636, Progression of Chronic Kidney Disease in Alport Syndrome: Interim Data from the ATHENA Study, Nov. 18, 2016, 1 page.
Gross et al., Kongress für Nephrologie, 8th Annual Meeting of the German Society of Nephrology, Oral Presentation, Rate of Progression in Renal Failure and Renal Biomarkers in Patients with Alport Syndrome: Interim Results from the prospective, non-interventional ATHENA Study, Sep. 10-13, 2016, 10 pages.
Grundy et al., "Nonclinical Pharmacokinetics and Toxicokinetics of RG-012, an Inhibitor of MicroRNA-21 Being Investigated for Treatment of Alport Syndrome," Kidney Week 2015 Poster, Nov. 7, 2015, 1 page.
Grundy et al., "Nonclinical Pharmacokinetics and Toxicokinetics of RG-012, an Inhibitor of MicroRNA-21 Being Investigated for Treatment of Alport Syndrome," Abstract SA-PO538, Kidney Week 2015, Oct. 2015, 1 page.
Grundy et al., ERA-EDTA 2016 Congress, Abstract SP257, Treatment with the MicroRNA-21 Inhibitor RG-012 Given with and without Ramipril Delays Renal Impairment Progression and Prolongs Survival when Initiated up to Chronic Kidney Disease (CKD) Stage 3 in a Mouse Model of Alport Syndrome, May 2016, 1 page.
Grundy et al., ERA-EDTA 2016 Congress, Abstract SP283, Renal Impairment Effects on Plasma and Tissue Exposure of Unconjugated and Galnac-conjugated Anti-miRs in a Chronic Kidney Disease (CKD) Mouse Model, May 2016, 1 page.
Grundy et al., ERA-EDTA 2016 Congress, Poster SP257, Treatment with the MicroRNA-21 Inhibitor RG-012 Given with and without Ramipril Delays Renal Impairment Progression and Prolongs Survival when Initiated up to Chronic Kidney Disease (CKD) Stage 3 in a Mouse Model of Alport Syndrome, May 2016, 1 page.
Grundy et al., ERA-EDTA 2016 Congress, Poster SP283, Renal Impairment Effects on Plasma and Tissue Exposure of Unconjugated and Galnac-conjugated Anti-miRs in a Chronic Kidney Disease (CKD) Mouse Model, May 2016, 1 page.
Grundy et al., Kidney Week 2016, Abstract SA-PO508, Safety and Pharmacokinetics in Healthy Human Volunteers of RG-012: An Inhibitor of MicroRNA-21 Being Investigated for Treatment of Alport Syndrome, Oct. 2016, 1 page.
Grundy et al., Kidney Week 2016, Poster SA-PO508, Safety and Pharmacokinetics in Healthy Human Volunteers of RG-012: An Inhibitor of MicroRNA-21 Being Investigated for Treatment of Alport Syndrome, Nov. 19, 2016, 1 page.
International Search Report and Written Opinion for PCT/US2012/034880, dated Jul. 25, 2012, 15 pages.
International Search Report and Written Opinion for PCT/US2012/037913, dated Aug. 21, 2013, 15 pages.
International Search Report and Written Opinion for PCT/US2013/063884, dated Jan. 16, 2014, 13 pages.
Chen et al., "Modem Genetic Testing and Clinical Practice," Shanghai Scientific and Technical Literature, 1999, p. 134.
Chen et al., "Modern Genetic Testing and Clinical Practice," Shanghai Scientific and Technical Literature, 1999, p. 134

*p=0.0008

SEQUENCE LISTING

```
<160> NUMBER OF SEQ ID NOS: 4

<210> SEQ ID NO 1
<211> LENGTH: 22
<212> TYPE: RNA
<213> ORGANISM: Homo sapiens

<400> SEQUENCE: 1
uagcuuauca gacugauguu ga                                              22

<210> SEQ ID NO 2
<211> LENGTH: 72
<212> TYPE: RNA
<213> ORGANISM: Homo sapiens

<400> SEQUENCE: 2
ugucggguag cuuaucagac ugauguugac uguugaaucu cauggcaaca ccagucgaug     60
ggcugucuga ca                                                         72

<210> SEQ ID NO 3
<211> LENGTH: 19
<212> TYPE: DNA
```

```
<213> ORGANISM: Artificial sequence
<220> FEATURE:
<223> OTHER INFORMATION: Synthetic

<400> SEQUENCE: 3
acatcagtct gataagcta                                                19

<210> SEQ ID NO 4
<211> LENGTH: 15
<212> TYPE: DNA
<213> ORGANISM: Artificial sequence
<220> FEATURE:
<223> OTHER INFORMATION: Synthetic

<400> SEQUENCE: 4
caatctaata agcta                                                    15
```

METHODS FOR TREATMENT OF ALPORT SYNDROME

This application is a continuation of U.S. application Ser. No. 15/151,290, filed May 10, 2016, which is a continuation of U.S. application Ser. No. 14/677,387, filed Apr. 2, 2015, now U.S. Pat. No. 9,359,609, which is a continuation of U.S. application Ser. No. 14/048,827, filed Oct. 8, 2013, now U.S. Pat. No. 9,012,423, which claims the benefit of U.S. Provisional Application No. 61/711,514, filed Oct. 9, 2012, and U.S. Provisional Application No. 61/779,137, filed Mar. 13, 2013, each of which is incorporated by reference herein in its entirety for any purpose.

FIELD OF INVENTION

Provided herein are methods and compositions for the treatment of Alport Syndrome.

DESCRIPTION OF RELATED ART

Type IV collagen, a major component of the basement membrane, is a family of six alpha chains: alpha-1 collagen (Type IV), alpha-2 collagen (Type IV), alpha-3 collagen (Type IV), alpha-4 collagen (Type IV), alpha-5 collagen (Type IV), and alpha-6 collagen (Type IV). The alpha-3, alpha-4 and alpha-6 chains of collagen IV are fundamental components of the collagen network of the glomerular basement membrane (GBM), which performs the critical function of filtration of blood by the kidney.

Alport Syndrome is an inherited form of kidney disease in which an abnormal type of glomerular basement membrane (GBM) is produced, leading to interstitial fibrosis, glomerular sclerosis and eventual loss of kidney function. The disease is also frequently characterized by hearing defects and ocular anomalies. Alport Syndrome is caused by a mutation in Col4a3, Col4a4, or Col4a5, which encode the alpha3(IV), alpha4(IV), and alpha5(IV) chains of type IV collagen, respectively. Mutations in the Col4a5 gene on the X chromosome cause the X-linked form of Alport Syndrome, which accounts for 85% of all cases of the disease. An autosomal recessive form is due to inheritance of mutations in each copy of either Col4a3 or Col4a4, each of which is located on chromosome 2. The rare autosomal dominant form is due to inheritance of a dominant-negative mutation in either the Col4a3 or Col4a4 gene. The X-linked form is more severe in males than in females, with most cases in males progressing to end-stage renal disease (ESRD). The autosomal form is of similar severity in males and females. Most cases of the disease are due to an inherited mutation, but some cases are due to a de novo mutation in one of the Col4aA genes.

SUMMARY OF INVENTION

Provided here are methods for treating Alport Syndrome comprising administering to a subject having or suspected of having Alport Syndrome a modified oligonucleotide consisting of 12 to 25 linked nucleosides, wherein the nucleobase sequence of the modified oligonucleotide is complementary to miR-21. In certain embodiments, the subject has been diagnosed as having Alport Syndrome prior to administering the modified oligonucleotide. In certain embodiments, the subject, prior to administration of the modified oligonucleotide, was determined to have an increased level of miR-21 in the kidney tissue of the subject. In certain embodiments, the subject, prior to administration of the modified oligonucleotide, was determined to have an increased level of miR-21 in the urine or blood of the subject.

In any of the embodiments provided herein, administration of a modified oligonucleotide complementary to miR-21, to a subject having or suspected of having Alport Syndrome, may improve kidney function; delay the onset of end stage renal disease; delay time to dialysis; delay time to renal transplant; and/or improve life expectancy in the subject.

In any of the embodiments provided herein, administration of a modified oligonucleotide complementary to miR-21, to a subject having or suspected of having Alport Syndrome may reduce hematuria; delay the onset of hematuria; reduce proteinuria; delay the onset of proteinuria; reduce kidney fibrosis; slow further progression of fibrosis; and/or halt further progression of fibrosis.

In any of the embodiments provided herein, the subject may have a mutation selected from a mutation in the gene encoding the alpha 3 chain of type IV collagen, a mutation in the gene encoding the alpha 4 chain of type IV collagen, or a mutation in the gene encoding the alpha 5 chain of type IV collagen. In certain embodiments, the subject is male. In certain embodiments, the subject is female. In certain embodiments, the subject is identified as having hematuria, and/or proteinuria. In certain embodiments, the subject has reduced kidney function. In certain embodiments, the subject is in need of improved kidney function.

Any of the embodiments provided herein may comprise measuring blood urea nitrogen in the blood of the subject; measuring creatinine in the blood of the subject; measuring creatinine clearance in the subject; measuring proteinuria in the subject; measuring albumin:creatinine ratio in the subject; and/or measuring glomerular filtration rate in the subject.

Any of the embodiments provided herein may comprise measuring N-acetyl-β-D-glucosaminidase (NAG) protein in the urine of the subject; measuring neutrophil gelatinase-associated lipocalin (NGAL) protein in the urine of the subject; measuring kidney injury molecule-1 (KIM-1) protein in the urine of the subject; measuring interleukin-18 (IL-18) protein in the urine of the subject; measuring monocyte chemoattractant protein (MCP1) levels in the urine of the subject; measuring connective tissue growth factor (CTGF) levels in the urine of the subject; measuring collagen IV (Col IV) fragments in the urine of the subject; measuring collagen III (Col III) fragments in the urine of the subject; and/or measuring podocyte protein levels in the urine of the subject, wherein the podocyte protein is selected from nephrin and podocin. Any of the embodiments provided herein may comprise measuring cystatin C protein in the blood of a subject; measuring β-trace protein (BTP) in the blood of a subject; and measuring 2-microglobulin (B2M) in the blood of a subject.

Any of the methods provided herein may improve one or more markers of kidney function in the subject, selected from reduced blood urea nitrogen in the subject; reduced creatinine in the blood of the subject; improved creatinine clearance in the subject; reduced proteinuria in the subject; reduced albumin:creatinine ratio in the subject; and/or improved glomerular filtration rate in the subject. Any of the methods provided herein may improve one or more markers of kidney function in the subject, selected from reduced NAG in the urine of the subject; reduced NGAL in the urine of the subject; reduced KIM-1 in the urine of the subject; reduced IL-18 in the urine of the subject; reduced MCP1 in the urine of the subject; reduced CTGF in the urine of the subject; reduced collagen IV fragments in the urine of the subject; reduced collagen III fragments in the urine of the subject; and reduced podocyte protein levels in the urine of the subject, wherein the podocyte protein is selected from nephrin and podocin. Any of the methods provided herein may improve one or more markers of kidney function selected from reduced cystatin C protein in the blood of a subject, reduced β-trace protein (BTP) in the blood of a subject, and reduced 2-microglobulin (B2M) in the blood of a subject.

In any of the embodiments provided herein, the proteinuria is albuminuria. The albuminuria may be high normal albuminuria, microalbuminuria, or macroalbuminuria.

In certain embodiments, the Alport Syndrome is the X-linked form of Alport Syndrome. In certain embodiments, the Alport Syndrome is the autosomal form of Alport Syndrome.

Any of the embodiments provided herein may comprise administering at least one additional therapy selected from an angiotensin II converting enzyme (ACE) inhibitor, an angiotensin II receptor blocker (ARB), an anti-hypertensive agent, a vitamin D analog, an oral phosphate binder, dialysis, and kidney transplant. In any of these embodiments, the angiotensin II converting enzyme (ACE) inhibitors is selected from captopril, enalapril, lisinopril, benazepril, quinapril, fosinopril, and ramipril. In any of these embodiments, the angiotensin II receptor blockers (ARB) is selected from candesartan, irbesartan, olmesartan, losartan, valsartan, telmisartan, and eprosartan. In any of these embodiments, an ACE inhibitor is selected from cilazapril, perindopril, and trandolapril.

In certain embodiments, an ACE inhibitor is administered at a dose ranging from 0.5 to 1 mg/m²/day, from 1 to 6 mg/m²/day, from 1 to 2 mg/m²/day, from 2 to 4 mg/m²/day, or from 4 to 8 mg/m²/day.

In certain embodiments, an ARB is administered at a dose ranging from 6.25 to 150 mg/m2/day. In any of these embodiments, an ARB is administered at a dose of 6.25 mg/m²/day, 10 mg/m²/day, 12.5 mg/m²/day, 18.75 mg/m²/day, 37.5 mg/m²/day, 50 mg/m²/day, or 150 mg/m²/day.

In certain embodiments, the at least one additional therapy is an aldosterone antagonsist. In certain embodiments, an aldosterone antagonist is spironolactone. In certain embodiments, spironolactone is administered at a dose ranging from 10 to 35 mg daily. In certain embodiments, spironolactone is administered at a dose of 25 mg daily.

In any of the embodiments provided herein, the nucleobase sequence of the modified oligonucleotide is at least 90% complementary, is at least 95% complementary, or is 100% complementary to the nucleobase sequence of miR-21 (SEQ ID NO: 1).

In any of the embodiments provided herein, the modified oligonucleotide consists of 8 to 30, 12 to 25, or 15 to 25 linked nucleosides. In any of the embodiments provided herein, the modified oligonucleotide consists of 12, 13, 14, 15, 16, 17, 18, 19, 20, 21, or 22 linked nucleosides. In any of the embodiments provided herein, the modified oligonucleotide consists of 15, 16, 17, 18, 19, 20, 21, or 22 linked nucleosides.

In any of the embodiments provided herein, the modified oligonucleotide comprises at least one modified nucleoside. The modified nucleoside may be selected from an S-cEt nucleoside, a 2'—O-methoxyethyl nucleoside, and an LNA nucleoside. The modified oligonucleotide may comprise at least one modified internucleoside linkage. Each internucleoside linkage of the modified oligonucleotide may be a modified internucleoside linkage. In certain embodiments, the modified internucleoside linkage is a phosphorothioate internucleoside linkage.

In any of the embodiments provided herein, the modified oligonucleotide may have the structure 5'-$A_E C_S ATC_S AGTC_S TGAU_S AAGC_S TA_E$-3', (SEQ ID NO: 3) where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides, and each internucleoside linkage is a phosphorothioate internucleoside linkage.

Provided herein is the use of a modified oligonucleotide consisting of 8 to 30, 12 to 25, or 15 to 25 linked nucleosides, wherein the nucleobase sequence of the modified oligonucleotide is complementary to miR-21, for the treatment of Alport Syndrome.

DETAILED DESCRIPTION

Figure 1A:
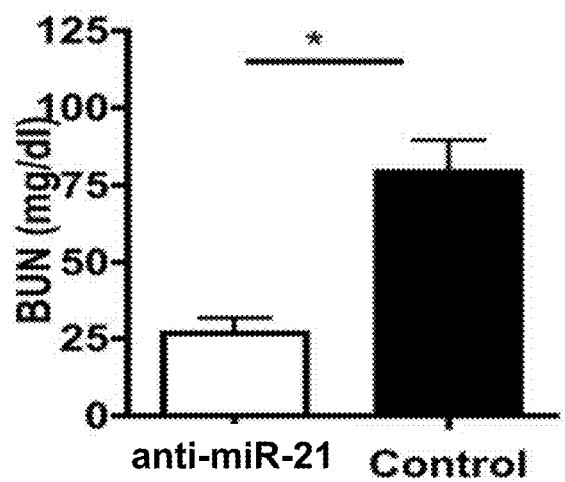
FIG. 1A-B. Anti-miR-21 improves kidney function of Col4a3−/−mice. Blood urea nitrogen (BUN) at 9 weeks (A) and urinary albumin/creatinine ratio at weeks 3, 5, 7 and 9 (B). * indicates statistical significance.

Unless defined otherwise, all technical and scientific terms used herein have the same meaning as is commonly understood by one of skill in the arts to which the invention belongs. Unless specific definitions are provided, the nomenclature utilized in connection with, and the procedures and techniques of, analytical chemistry, synthetic organic chemistry, and medicinal and pharmaceutical chemistry described herein are those well-known and commonly used in the art. In the event that there is a plurality of definitions for terms herein, those in this section prevail. Standard techniques may be used for chemical synthesis, chemical analysis, pharmaceutical preparation, formulation and delivery, and treatment of subjects. Certain such techniques and procedures may be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose. Where permitted, all patents, patent applications, published applications and publications, GENBANK sequences, websites and other published materials referred to throughout the entire disclosure herein, unless noted otherwise, are incorporated by reference in their entirety. Where reference is made to a URL or other such identifier or address, it is understood that such identifiers can change and particular information on the internet can change, but equivalent information can be found by searching the internet. Reference thereto evidences the availability and public dissemination of such information.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Definitions

"Alport Syndrome" means an inherited form of kidney disease in which an abnormal level of glomerular basement membrane (GBM) is produced, leading to interstitial fibrosis, glomerular sclerosis and eventual loss of kidney function. The disease is also frequently characterized by hearing defects and ocular anomalies.

"Hematuria" means the presence of red blood cells in the urine.

"Albuminuria" means the presence of excess albumin in the urine, and includes without limitation, normal albuminuria, high normal albuminuria, microalbuminuria and macroalbuminuria. Normally, the glomerular filtration permeability barrier, which is composed of podocyte, glomerular basement membrane and endothelial cells, prevents serum protein from leaking into urine. Albuminuria may reflect injury of the glomerular filtration permeability barrier. Albuminuria may be calculated from a 24-hour urine sample, an overnight urine sample or a spot-urine sample.

"High normal albuminuria" means elevated albuminuria characterized by (i) the excretion of 15 to <30 mg of albumin into the urine per 24 hours and/or (ii) an albumin/creatinine ratio of 1.25 to <2.5 mg/mmol (or 10 to <20 mg/g) in males or 1.75 to <3.5 mg/mmol (or 15 to <30 mg/g) in females.

"Microalbuminuria" means elevated albuminuria characterized by (i) the excretion of 30 to 300 mg of albumin into the urine per 24 hours and/or (ii) an albumin/creatinine ratio of 2.5 to <25 mg/mmol (or 20 to <200 mg/g) in males or 3.5 to <35 mg/mmol (or 30 to <300 mg/g) in females.

"Macroalbuminuria" means elevated albuminuria characterized by the excretion of more than 300 mg of albumin into the urine per 24 hours and/or (ii) an albumin/creatinine ratio of >25 mg/mmol (or >200 mg/g) in males or >35 mg/mmol (or >300 mg/g) in females.

"Albumin/creatinine ratio" means the ratio of urine albumin (mg/dL) per urine creatinine (g/dL) and is expressed as mg/g. In certain embodiments, albumin/creatinine ratio may be calculated from a spot-urine sample and may be used as an estimate of albumin excretion over a 24 hour period.

"Estimated glomerular filtration rate (eGFR)" or "glomerular filtration rate (GFR)" means a measurement of how well the kidneys are filtering creatinine, and is used as an estimate of how much blood passes through the glomeruli per minute. Normal results may range from 90-120 mL/min/1.73 $m^2$. Levels below 60 mL/min/1.73 $m^2$ for 3 or more months may be an indicator chronic kidney disease. Levels below 15 mL/min/1.73 $m^2$ may be an indicator of kidney failure.

"Proteinuria" means the presence of an excess of serum proteins in the urine. Proteinuria may be characterized by the excretion of >250 mg of protein into the urine per 24 hours and/or a urine protein to creatinine ratio of ≥0.20 mg/mg. Serum proteins elevated in association with proteinuria include, without limitation, albumin.

"Blood urea nitrogen" or "BUN" means a measure of the amount of nitrogen in the blood in the form of urea. The liver produces urea in the urea cycle as a waste product of the digestion of protein, and the urea is removed from the blood by the kidneys. Normal human adult blood may contain between 7 to 21 mg of urea nitrogen per 100 ml (7-21 mg/dL) of blood. Measurement of blood urea nitrogen is used as an indicator of renal health. If the kidneys are not able to remove urea from the blood normally, a subject's BUN rises.

"End stage renal disease (ESRD)" means the complete or almost complete failure of kidney function.

"Impaired kidney function" means reduced kidney function, relative to normal kidney function.

"Fibrosis" means the formation or development of excess fibrous connective tissue in an organ or tissue. In certain embodiments, fibrosis occurs as a reparative or reactive process. In certain embodiments, fibrosis occurs in response to damage or injury. The term "fibrosis" is to be understood as the formation or development of excess fibrous connective tissue in an organ or tissue as a reparative or reactive process, as opposed to a formation of fibrous tissue as a normal constituent of an organ or tissue.

"Slows further progression" means to reduce the rate at which a medical condition moves towards an advanced state.

"Halts further progression" means to stop progression of a medical condition to an advanced state.

"Delay time to dialysis" means to maintain sufficient kidney function such that the need for dialysis treatment is delayed.

"Delay time to renal transplant" means to maintain sufficient kidney function such that the need for a kidney transplant is delayed.

"Improves life expectancy" means to lengthen the life of a subject by treating one or more symptoms of a disease in the subject.

"Anti-miR" means an oligonucleotide having a nucleobase sequence complementary to a microRNA. In certain embodiments, an anti-miR is a modified oligonucleotide.

"Anti-miR-X" where "miR-X" designates a particular microRNA, means an oligonucleotide having a nucleobase sequence complementary to miR-X. In certain embodiments, an anti-miR-X is fully complementary (i.e., 100% complementary) to miR-X. In certain embodiments, an anti-miR-X is at least 80%, at least 85%, at least 90%, or at least 95% complementary to miR-X. In certain embodiments, an anti-miR-X is a modified oligonucleotide.

"miR-21" means the mature miRNA having the nucleobase sequence UAGCUUAUCAGACUGAUGUUGA (SEQ ID NO: 1).

"miR-21 stem-loop sequence" means the stem-loop sequence having the nucleobase sequence UGUCGGGUAGCUUAUCAGACUGAUGUUGACUGUUGAAUCUCAUGGCAACACCAGUCGAU GGGCUGUCUGACA (SEQ ID NO: 2).

"Target nucleic acid" means a nucleic acid to which an oligomeric compound is designed to hybridize.

"Targeting" means the process of design and selection of nucleobase sequence that will hybridize to a target nucleic acid.

"Targeted to" means having a nucleobase sequence that will allow hybridization to a target nucleic acid.

"Modulation" means a perturbation of function, amount, or activity. In certain embodiments, modulation means an increase in function, amount, or activity. In certain embodiments, modulation means a decrease in function, amount, or activity.

"Expression" means any functions and steps by which a gene's coded information is converted into structures present and operating in a cell.

"Nucleobase sequence" means the order of contiguous nucleobases in an oligomeric compound or nucleic acid, typically listed in a 5' to 3' orientation, independent of any sugar, linkage, and/or nucleobase modification.

"Contiguous nucleobases" means nucleobases immediately adjacent to each other in a nucleic acid.

"Nucleobase complementarity" means the ability of two nucleobases to pair non-covalently via hydrogen bonding.

"Complementary" means that one nucleic acid is capable of hybridizing to another nucleic acid or oligonucleotide. In certain embodiments, complementary refers to an oligonucleotide capable of hybridizing to a target nucleic acid.

"Fully complementary" means each nucleobase of an oligonucleotide is capable of pairing with a nucleobase at each corresponding position in a target nucleic acid. In certain embodiments, an oligonucleotide is fully complementary to a microRNA, i.e. each nucleobase of the oligonucleotide is complementary to a nucleobase at a corresponding position in the microRNA. In certain embodiments, an oligonucleotide wherein each nucleobase has complementarity to a nucleobase within a region of a microRNA stem-loop sequence is fully complementary to the microRNA stem-loop sequence.

"Percent complementarity" means the percentage of nucleobases of an oligonucleotide that are complementary to an equal-length portion of a target nucleic acid. Percent complementarity is calculated by dividing the number of nucleobases of the oligonucleotide that are complementary to nucleobases at corresponding positions in the target nucleic acid by the total number of nucleobases in the oligonucleotide.

"Percent identity" means the number of nucleobases in a first nucleic acid that are identical to nucleobases at corresponding positions in a second nucleic acid, divided by the total number of nucleobases in the first nucleic acid. In certain embodiments, the first nucleic acid is a microRNA and the second nucleic acid is a microRNA. In certain embodiments, the first nucleic acid is an oligonucleotide and the second nucleic acid is an oligonucleotide.

"Hybridize" means the annealing of complementary nucleic acids that occurs through nucleobase complementarity.

"Mismatch" means a nucleobase of a first nucleic acid that is not capable of Watson-Crick pairing with a nucleobase at a corresponding position of a second nucleic acid.

"Identical" in the context of nucleobase sequences, means having the same nucleobase sequence, independent of sugar, linkage, and/or nucleobase modifications and independent of the methyl state of any pyrimidines present.

"MicroRNA" means an endogenous non-coding RNA between 18 and 25 nucleobases in length, which is the product of cleavage of a pre-microRNA by the enzyme Dicer. Examples of mature microRNAs are found in the microRNA database known as miRBase (http://microrna.sanger.ac.uk/). In certain embodiments, microRNA is abbreviated as "microRNA" or "miR."

"Pre-microRNA" or "pre-miR" means a non-coding RNA having a hairpin structure, which is the product of cleavage of a pri-miR by the double-stranded RNA-specific ribonuclease known as Drosha.

"Stem-loop sequence" means an RNA having a hairpin structure and containing a mature microRNA sequence. Pre-microRNA sequences and stem-loop sequences may overlap. Examples of stem-loop sequences are found in the microRNA database known as miRBase (http://microrna.sanger.ac.uk/).

"Pri-microRNA" or "pri-miR" means a non-coding RNA having a hairpin structure that is a substrate for the double-stranded RNA-specific ribonuclease Drosha.

"microRNA precursor" means a transcript that originates from a genomic DNA and that comprises a non-coding, structured RNA comprising one or more microRNA sequences. For example, in certain embodiments a microRNA precursor is a pre-microRNA. In certain embodiments, a microRNA precursor is a pri-microRNA.

"microRNA-regulated transcript" means a transcript that is regulated by a microRNA.

"Seed sequence" means a nucleobase sequence comprising from 6 to 8 contiguous nucleobases of nucleobases 1 to 9 of the 5'-end of a mature microRNA sequence.

"Seed match sequence" means a nucleobase sequence that is complementary to a seed sequence, and is the same length as the seed sequence.

"Oligomeric compound" means a compound that comprises a plurality of linked monomeric subunits. Oligomeric compounds included oligonucleotides.

"Oligonucleotide" means a compound comprising a plurality of linked nucleosides, each of which can be modified or unmodified, independent from one another.

"Naturally occurring internucleoside linkage" means a 3' to 5' phosphodiester linkage between nucleosides.

"Natural sugar" means a sugar found in DNA (2' —H) or RNA (2' —OH).

"Internucleoside linkage" means a covalent linkage between adjacent nucleosides.

"Linked nucleosides" means nucleosides joined by a covalent linkage.

"Nucleobase" means a heterocyclic moiety capable of non-covalently pairing with another nucleobase.

"Nucleoside" means a nucleobase linked to a sugar moiety.

"Nucleotide" means a nucleoside having a phosphate group covalently linked to the sugar portion of a nucleoside.

"Compound comprising a modified oligonucleotide consisting of" a number of linked nucleosides means a compound that includes a modified oligonucleotide having the specified number of linked nucleosides. Thus, the compound may include additional substituents or conjugates. Unless otherwise indicated, the compound does not include any additional nucleosides beyond those of the modified oligonucleotide.

"Modified oligonucleotide" means an oligonucleotide having one or more modifications relative to a naturally occurring terminus, sugar, nucleobase, and/or internucleoside linkage. A modified oligonucleotide may comprise unmodified nucleosides.

"Single-stranded modified oligonucleotide" means a modified oligonucleotide which is not hybridized to a complementary strand.

"Modified nucleoside" means a nucleoside having any change from a naturally occurring nucleoside. A modified nucleoside may have a modified sugar and an unmodified nucleobase. A modified nucleoside may have a modified sugar and a modified nucleobase. A modified nucleoside may have a natural sugar and a modified nucleobase. In certain embodiments, a modified nucleoside is a bicyclic nucleoside. In certain embodiments, a modified nucleoside is a non-bicyclic nucleoside.

"Modified internucleoside linkage" means any change from a naturally occurring internucleoside linkage.

"Phosphorothioate internucleoside linkage" means a linkage between nucleosides where one of the non-bridging atoms is a sulfur atom.

"Modified sugar moiety" means substitution and/or any change from a natural sugar.

"Unmodified nucleobase" means the naturally occurring heterocyclic bases of RNA or DNA: the purine bases adenine (A) and guanine (G), and the pyrimidine bases thymine (T), cytosine (C) (including 5-methylcytosine), and uracil (U).

"5-methylcytosine" means a cytosine comprising a methyl group attached to the 5 position.

"Non-methylated cytosine" means a cytosine that does not have a methyl group attached to the 5 position.

"Modified nucleobase" means any nucleobase that is not an unmodified nucleobase.

"Sugar moiety" means a naturally occurring furanosyl or a modified sugar moiety.

"Modified sugar moiety" means a substituted sugar moiety or a sugar surrogate.

"2'—O-methyl sugar" or "2'—OMe sugar" means a sugar having a O-methyl modification at the 2' position.

"2'—O-methoxyethyl sugar" or "2'-MOE sugar" means a sugar having a O-methoxyethyl modification at the 2' position.

"2'-fluoro" or "2'—F" means a sugar having a fluoro modification of the 2' position.

"Bicyclic sugar moiety" means a modified sugar moiety comprising a 4 to 7 membered ring (including by not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl. Nonlimiting exemplary bicyclic sugar moieties include LNA, ENA, cEt, S-cEt, and R-cEt.

"Locked nucleic acid (LNA) sugar moiety" means a substituted sugar moiety comprising a $(CH_2)$—O bridge between the 4' and 2' furanose ring atoms.

"ENA sugar moiety" means a substituted sugar moiety comprising a $(CH_2)_2$—O bridge between the 4' and 2' furanose ring atoms.

"Constrained ethyl (cEt) sugar moiety" means a substituted sugar moiety comprising a $CH(CH_3)$—O bridge between the 4' and the 2' furanose ring atoms. In certain embodiments, the $CH(CH_3)$—O bridge is constrained in the S orientation. In certain embodiments, the $(CH_2)_2$—O is constrained in the R orientation.

"S-cEt sugar moiety" means a substituted sugar moiety comprising an S-constrained $CH(CH_3)$—O bridge between the 4' and the 2' furanose ring atoms.

"R-cEt sugar moiety" means a substituted sugar moiety comprising an R-constrained $CH(CH_3)$—O bridge between the 4' and the 2' furanose ring atoms.

"2'—O-methyl nucleoside" means a 2'-modified nucleoside having a 2'—O-methyl sugar modification.

"2'—O-methoxyethyl nucleoside" means a 2'-modified nucleoside having a 2'—O-methoxyethyl sugar modification. A 2'—O-methoxyethyl nucleoside may comprise a modified or unmodified nucleobase.

"2'-fluoro nucleoside" means a 2'-modified nucleoside having a 2'-fluoro sugar modification. A 2'-fluoro nucleoside may comprise a modified or unmodified nucleobase.

"Bicyclic nucleoside" means a 2'-modified nucleoside having a bicyclic sugar moiety. A bicyclic nucleoside may have a modified or unmodified nucleobase.

"cEt nucleoside" means a nucleoside comprising a cEt sugar moiety. A cEt nucleoside may comprise a modified or unmodified nucleobase.

"S-cEt nucleoside" means a nucleoside comprising an S-cEt sugar moiety.

"R-cEt nucleoside" means a nucleoside comprising an R-cEt sugar moiety.

"β-D-deoxyribonucleoside" means a naturally occurring DNA nucleoside.

"β-D-ribonucleoside" means a naturally occurring RNA nucleoside.

"LNA nucleoside" means a nucleoside comprising a LNA sugar moiety.

"ENA nucleoside" means a nucleoside comprising an ENA sugar moiety.

"Subject" means a human or non-human animal selected for treatment or therapy.

"Subject in need thereof" means a subject that is identified as in need of a therapy or treatment.

"Subject suspected of having" means a subject exhibiting one or more clinical indicators of a disease.

"Administering" means providing a pharmaceutical agent or composition to a subject, and includes, but is not limited to, administering by a medical professional and self-administering.

"Parenteral administration" means administration through injection or infusion. Parenteral administration includes, but is not limited to, subcutaneous administration, intravenous administration, and intramuscular administration.

"Subcutaneous administration" means administration just below the skin.

"Intravenous administration" means administration into a vein.

"Administered concomitantly" refers to the co-administration of two or more agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Duration" means the period of time during which an activity or event continues. In certain embodiments, the duration of treatment is the period of time during which doses of a pharmaceutical agent or pharmaceutical composition are administered.

"Therapy" means a disease treatment method. In certain embodiments, therapy includes, but is not limited to, chemotherapy, radiation therapy, or administration of a pharmaceutical agent.

"Treatment" means the application of one or more specific procedures used for the cure or amelioration of a disease. In certain embodiments, the specific procedure is the administration of one or more pharmaceutical agents.

"Ameliorate" means to lessen the severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

"At risk for developing" means the state in which a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

"Prevent the onset of" means to prevent the development of a condition or disease in a subject who is at risk for developing the disease or condition. In certain embodiments, a subject at risk for developing the disease or condition receives treatment similar to the treatment received by a subject who already has the disease or condition.

"Delay the onset of" means to delay the development of a condition or disease in a subject who is at risk for developing the disease or condition. In certain embodiments, a subject at risk for developing the disease or condition receives treatment similar to the treatment received by a subject who already has the disease or condition.

"Therapeutic agent" means a pharmaceutical agent used for the cure, amelioration or prevention of a disease.

"Dose" means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual. In certain embodiments, a dose is administered as a slow infusion.

"Dosage unit" means a form in which a pharmaceutical agent is provided. In certain embodiments, a dosage unit is a vial containing lyophilized oligonucleotide. In certain embodiments, a dosage unit is a vial containing reconstituted oligonucleotide.

"Therapeutically effective amount" refers to an amount of a pharmaceutical agent that provides a therapeutic benefit to an animal.

"Pharmaceutical composition" means a mixture of substances suitable for administering to an individual that includes a pharmaceutical agent. For example, a pharmaceutical composition may comprise a sterile aqueous solution.

"Pharmaceutical agent" means a substance that provides a therapeutic effect when administered to a subject.

"Active pharmaceutical ingredient" means the substance in a pharmaceutical composition that provides a desired effect.

"Improved organ function" means a change in organ function toward normal limits. In certain embodiments, organ function is assessed by measuring molecules found in a subject's blood or urine. For example, in certain embodiments, improved kidney function is measured by a reduction in blood urea nitrogen, a reduction in proteinuria, a reduction in albuminuria, etc.

"Acceptable safety profile" means a pattern of side effects that is within clinically acceptable limits.

"Side effect" means a physiological response attributable to a treatment other than desired effects. In certain embodiments, side effects include, without limitation, injection site reactions, liver function test abnormalities, kidney function abnormalities, liver toxicity, renal toxicity, central nervous system abnormalities, and myopathies. Such side effects may be detected directly or indirectly. For example, increased aminotransferase levels in serum may indicate liver toxicity or liver function abnormality. For example, increased bilirubin may indicate liver toxicity or liver function abnormality.

"Subject compliance" means adherence to a recommended or prescribed therapy by a subject.

"Comply" means the adherence with a recommended therapy by a subject.

"Recommended therapy" means a treatment recommended by a medical professional for the treatment, amelioration, or prevention of a disease.

The term "blood" as used herein, encompasses whole blood and blood fractions, such as serum and plasma.

Overview

Alport Syndrome is an inherited form of kidney disease in which an abnormal level of glomerular basement membrane (GBM) is produced, leading to interstitial fibrosis, glomerular sclerosis and typically leads to end-stage renal disease. In the management of Alport Syndrome, the primary goal for treatment is to maintain kidney function and prevent the onset of end-stage renal disease (ESRD), which in turn improves life expectancy of subjects with Alport Syndrome.

Alport Syndrome is characterized by progressive fibrosis due to defects in GBM composition, thus improvements in GBM morphology and function are desirable. It is demonstrated herein that modified oligonucleotide targeted to miR-21 improves kidney function in an experimental model of Alport Syndrome. Additionally, glomerular sclerosis and fibrosis are reduced following anti-miR-21 treatment. It is further demonstrated herein that anti-miR-21 improves survival in an experimental model of Alport Syndrome. As such, these modified oligonucleotides targeted to miR-21 are useful for the treatment of Alport Syndrome.

Certain Uses of the Invention

Provided herein are methods for the treatment of Alport Syndrome, comprising administering to a subject having or suspected of having Alport Syndrome a modified oligonucleotide complementary to miR-21.

In certain embodiments, the subject has been diagnosed as having Alport Syndrome prior to administration of the modified oligonucleotide. Diagnosis of Alport Syndrome may be achieved through evaluation of parameters including, without limitation, a subject's family history, clinical features (including without limitation proteinuria, albuminuria, hematuria, impaired GFR, deafness and/or ocular changes) and results of tissue biopsies. Kidney biopsies may be tested for the presence or absence of the type IV collagen alpha-3, alpha-4, and alpha-5 chains. Additionally, structural changes in the glomerulus can be detected by electron microscopy of kidney biopsy material. A skin biopsy may be tested for the presence of the type IV collagen alpha-5 chain, which is normally present in skin and almost always absent from male subjects with the X-linked form of Alport Syndrome. Diagnosis of Alport Syndrome may also include screening for mutations in one or more of the Col4a3, Col4a4, or Col4a5 genes.

In certain embodiments, levels of miR-21 are increased in the kidney of a subject having Alport Syndrome. In certain embodiments, prior to administration, a subject is determined to have an increased level of miR-21 in the kidney. miR-21 levels may be measured from kidney biopsy material. In certain embodiments, prior to administration, a subject is determined to have an increased level of miR-21 in the urine or blood of the subject.

In certain embodiments, administration of a modified oligonucleotide complementary to miR-21 results in one or more clinically beneficial outcomes. In certain embodiments, the administration improves kidney function. In certain embodiments, the administration delays the onset of end-stage renal disease. In certain embodiments, the administration delays time to dialysis. In certain embodiments, the administration delays time to renal transplant. In certain embodiments, the administration improves life expectancy of the subject.

In certain embodiments, the administering reduces kidney fibrosis. In certain embodiments the administering slows further progression of kidney fibrosis. In certain embodiments, the administration halts further progression of kidney fibrosis. In certain embodiments, the administration reduces hematuria. In certain embodiments, the administration delays the onset of hematuria. In certain embodiments, the administration reduces proteinuria. In certain embodiments, the administration delays the onset of proteinuria.

The subject having or suspected of having Alport Syndrome may have a mutation in the gene encoding the alpha 3 chain of type IV collagen (Col4a3), a mutation in the gene encoding the alpha 4 chain of type IV collagen (Col4a4), or a mutation in the gene encoding the alpha 5 chain of type IV collagen (Col4a5). In certain embodiments, the subject is male. In certain embodiments, the subject is female.

In certain embodiments the subject has impaired kidney function. In certain embodiments, the subject is in need of improved kidney function. In certain embodiments, the subject is identified as having impaired kidney function. In certain embodiments, the subject is identified as having hematuria. In certain embodiments, the subject is identified as having proteinuria.

In any of the embodiments provided herein, a subject may be subjected to certain tests to evaluate kidney function. Such tests include, without limitation, measurement of blood urea nitrogen in the subject; measuring creatinine in the blood of the subject; measuring creatinine clearance in the blood of the subject; measuring proteinuria in the subject; measuring albumin:creatinine ratio in the subject; measuring glomerular filtration rate in the subject; and measuring urinary output in the subject.

In any of the embodiments provided herein, proteins present in the urine or blood may be used to evaluate kidney function. Such tests of kidney function include, but are not limited to, measuring N-acetyl-β-D-glucosaminidase (NAG) protein in the urine of the subject; measuring neutrophil gelatinase-associated lipocalin (NGAL) protein in the urine of the subject; measuring kidney injury molecule-1 (KIM-1) protein in the urine of the subject; measuring interleukin-18 (IL-18) protein in the urine of the subject; measuring connective tissue growth factor (CTGF) levels in the urine of the subject; measuring monocyte chemoattractant protein 1 (MCP1) levels in the urine of the subject; measuring collagen IV (Col IV) fragments in the urine of the subject; measuring collagen III (Col III) fragment levels in the urine of the subject; measuring cystatin C protein in the blood of a subject; measuring β-trace protein (BTP) in the blood of a subject; and measuring 2-microglobulin (B2M) in the blood of a subject. In any of the embodiments provided herein, markers of podocyte injury can be measuring in the urine. Such proteins include nephrin and podocin. The proteins may be quantitated, for example, by enzyme-linked immunosorbent assay (ELISA), or radioimmunoassay (RIA) using commercially available kits.

In any of the embodiments provided herein, the administration of a modified oligonucleotide targeted to miR-21 improves one or more markers of kidney function in the subject. Improvements in markers of kidney function include, without limitation: reduced blood urea nitrogen in the subject; reduced creatinine in the blood of the subject; improved creatinine clearance in the subject; reduced proteinuria in the subject; reduced albumin:creatinine ratio in the subject; improved glomerular filtration rate in the subject; and/or increased urinary output in the subject.

Certain Additional Therapies

Treatments for Alport Syndrome or any of the conditions listed herein may comprise more than one therapy. As such, in certain embodiments provided herein are methods for treating a subject having or suspected of having Alport Syndrome comprising administering at least one therapy in addition to administering a modified oligonucleotide having a nucleobase sequence complementary to a miR-21.

In certain embodiments, the at least one additional therapy comprises a pharmaceutical agent.

In certain embodiments, pharmaceutical agents include angiotensin II receptor blockers (ARB). In certain embodiments, an angiotensin II receptor blocker is candesartan, irbesartan, olmesartan, losartan, valsartan, telmisartan, or eprosartan.

In certain embodiments, pharmaceutical agents include angiotensin II converting enzyme (ACE) inhibitors. In certain embodiments, an ACE inhibitor is captopril, enalapril, lisinopril, benazepril, quinapril, fosinopril, or ramipril.

In certain embodiments, a pharmaceutical agent is an anti-hypertensive agent. Anti-hypertensive agents are used to control blood pressure of the subject.

In certain embodiments, a pharmaceutical agent is a vitamin D analog. Vitamin D analogs may be used to limit the production of parathyroid hormone in the subject.

In certain embodiments, a pharmaceutical agent is an oral phosphate binder that reduces dietary phosphate absorption.

In certain embodiments, pharmaceutical agents include immunosuppressive agents. In certain embodiments, an immunosuppressive agent is a corticosteroid, cyclophosphamide, or mycophenolate mofetil.

In certain embodiments, a pharmaceutical agent is cyclosporine, an HMG-Coenzyme A inhibitor, a vasopeptidase inhibitor, or a TGF-beta-antagonist.

In certain embodiments, an additional therapy is gene therapy. In certain embodiments, the gene therapy provides a normal Col4a3 gene. In certain embodiments, the gene therapy provides a normal Col4a4 gene. In certain embodiments, the gene therapy provides a normal Col4a5 gene.

In certain embodiments, an additional therapy is dialysis. In certain embodiments, an additional therapy is renal transplant.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drug. In certain embodiments, a non-steroidal anti-inflammatory agent is ibuprofen, a COX-I inhibitor, or a COX-2 inhibitor.

In certain embodiments, a pharmaceutical agent is a pharmaceutical agent that blocks one or more responses to fibrogenic signals.

In certain embodiments, pharmaceutical agents include anti-diabetic agent. Antidiabetic agents include, but are not limited to, biguanides, glucosidase inhibitors, insulins, sulfonylureas, and thiazolidenediones.

Certain MicroRNA Nucleobase Sequences

The modified oligonucleotides described herein have a nucleobase sequence that is complementary to miR-21 (SEQ ID NO: 1), or a precursor thereof (SEQ ID NO: 2). In certain embodiments, each nucleobase of the modified oligonucleotide is capable of undergoing base-pairing with a nucleobase at each corresponding position in the nucleobase sequence of miR-21, or a precursor thereof. In certain embodiments the nucleobase sequence of a modified oligonucleotide may have one or more mismatched base pairs with respect to the nucleobase sequence of miR-21 or precursor sequence, and remains capable of hybridizing to its target sequence.

As the miR-21 sequence is contained within the miR-21 precursor sequence, a modified oligonucleotide having a nucleobase sequence complementary to miR-21 is also complementary to a region of the miR-21 precursor.

In certain embodiments, a modified oligonucleotide consists of a number of linked nucleosides that is equal to the length of miR-21.

In certain embodiments, the number of linked nucleosides of a modified oligonucleotide is less than the length of miR-21. A modified oligonucleotide having a number of linked nucleosides that is less than the length of miR-21, wherein each nucleobase of the modified oligonucleotide is complementary to each nucleobase at a corresponding position of miR-21, is considered to be a modified oligonucleotide having a nucleobase sequence that is fully complementary to a region of the miR-21 sequence. For example, a modified oligonucleotide consisting of 19 linked nucleosides, where each nucleobase is complementary to a corresponding position of miR-21 that is 22 nucleobases in length, is fully complementary to a 19 nucleobase region of miR-21. Such a modified oligonucleotide has 100% complementarity to a 19 nucleobase portion of miR-21, and is considered to be 100% complementary to miR-21.

In certain embodiments, a modified oligonucleotide comprises a nucleobase sequence that is complementary to a seed sequence, i.e. a modified oligonucleotide comprises a seed-match sequence. In certain embodiments, a seed sequence is a hexamer seed sequence. In certain such embodiments, a seed sequence is nucleobases 1-6 of miR-21. In certain such embodiments, a seed sequence is nucleobases 2-7 of miR-21. In certain such embodiments, a seed sequence is nucleobases 3-8 of miR-21. In certain embodiments, a seed sequence is a heptamer seed sequence. In certain such embodiments, a heptamer seed sequence is nucleobases 1-7 of miR-21. In certain such embodiments, a heptamer seed sequence is nucleobases 2-8 of miR-21. In certain embodiments, the seed sequence is an octamer seed sequence. In certain such embodiments, an octamer seed sequence is nucleobases 1-8 of miR-21. In certain embodiments, an octamer seed sequence is nucleobases 2-9 of miR-21.

In certain embodiments, a modified oligonucleotide has a nucleobase sequence having one mismatch with respect to the nucleobase sequence of miR-21, or a precursor thereof In certain embodiments, a modified oligonucleotide has a nucleobase sequence having two mismatches with respect to the nucleobase sequence of miR-21, or a precursor thereof. In certain such embodiments, a modified oligonucleotide has a nucleobase sequence having no more than two mismatches with respect to the nucleobase sequence of miR-21, or a precursor thereof In certain such embodiments, the mismatched nucleobases are contiguous. In certain such embodiments, the mismatched nucleobases are not contiguous.

In certain embodiments, the number of linked nucleosides of a modified oligonucleotide is greater than the length of miR-21. In certain such embodiments, the nucleobase of an additional nucleoside is complementary to a nucleobase of the miR-21 stem-loop sequence. In certain embodiments, the number of linked nucleosides of a modified oligonucleotide is one greater than the length of miR-21. In certain such embodiments, the additional nucleoside is at the 5' terminus of an oligonucleotide. In certain such embodiments, the additional nucleoside is at the 3' terminus of an oligonucleotide. In certain embodiments, the number of linked nucleosides of a modified oligonucleotide is two greater than the length of miR-21. In certain such embodiments, the two additional nucleosides are at the 5' terminus of an oligonucleotide. In certain such embodiments, the two additional nucleosides are at the 3' terminus of an oligonucleotide. In certain such embodiments, one additional nucleoside is located at the 5' terminus and one additional nucleoside is located at the 3' terminus of an oligonucleotide. In certain embodiments, a region of the oligonucleotide may be fully complementary to the nucleobase sequence of miR-21, but the entire modified oligonucleotide is not fully complementary to miR-21. For example, a modified oligonucleotide consisting of 24 linked nucleosides, where the nucleobases of nucleosides 1 through 22 are each complementary to a corresponding position of miR-21 that is 22 nucleobases in length, has a 22 nucleoside portion that is fully complementary to the nucleobase sequence of miR-21 and approximately 92% overall complementarity to the nucleobase sequence of miR-21.

Certain Modified Oligonucleotides

In certain embodiments, a modified oligonucleotide has the structure 5'-$A_E C_S ATC_S AGTC_S TGAU_S AAGC_S TA_E$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; and each internucleoside linkage is a phosphorothioate internucleoside linkage.

In certain embodiments, a modified oligonucleotide has the structure 5'-$A_E C_S ATC_S A_S GTC_S U_S GAU_S A_S AGC_S U_S A_E$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; and each internucleoside linkage is a phosphorothioate internucleoside linkage.

In certain embodiments, a modified oligonucleotide has the structure 5'-$^{Me}C_E A_S A_S T_E C_S U_S A_E A_E U_S A_S A_E G_E C_S T_E A_S$-3' (SEQ ID NO: 4), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; a superscript "Me" indicates a 5-methyl group on the base of the nucleoside; and each internucleoside linkage is a phosphorothioate internucleoside linkage.

In certain embodiments, a modified oligonucleotide has the structure 5'-$A_E C_S A_E T_E C_S A_E G_E T_E C_S TGAU_S AAGC_S U_S A_S$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; and each internucleoside linkage is a phosphorothioate internucleoside linkage.

In certain embodiments, a modified oligonucleotide comprises one or more 5-methylcytosines. In certain embodiments, each cytosine of a modified oligonucleotide comprises a 5-methylcytosine.

In certain embodiments, a modified oligonucleotide consists of 8 to 30 linked nucleosides. In certain embodiments, a modified oligonucleotide consists of 12 to 25 linked nucleosides. In certain embodiments, a modified oligonucleotide consists of 15 to 30 linked nucleosides. In certain embodiments, a modified oligonucleotide consists of 15 to 25 linked nucleosides. In certain embodiments, a modified oligonucleotide consists of 15 to 19 linked nucleosides. In certain embodiments, a modified oligonucleotide consists of 15 to 16 linked nucleosides. In certain embodiments, a modified oligonucleotide consists of 19 to 24 linked nucleosides. In certain embodiments, a modified oligonucleotide consists of 21 to 24 linked nucleosides.

In certain embodiments, a modified oligonucleotide consists of 8 linked nucleosides. In certain embodiments, a modified oligonucleotide consists of 9 linked nucleosides. In certain embodiments, a modified oligonucleotide consists of 10 linked nucleosides. In certain embodiments, a modified oligonucleotide consists of 11 linked nucleosides. In certain embodiments, a modified oligonucleotide consists of 12 linked nucleosides. In certain embodiments, a modified oligonucleotide consists of 13 linked nucleosides. In certain embodiments, a modified oligonucleotide consists of 14 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides.

Certain Modifications

In certain embodiments, oligonucleotides provided herein may comprise one or more modifications to a nucleobase, sugar, and/or internucleoside linkage, and as such is a modified oligonucleotide. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

Nucleosides comprising such bicyclic sugar moieties are referred to as bicyclic nucleosides or BNAs. In certain embodiments, bicyclic nucleosides include, but are not limited to, (A) α-L-Methyleneoxy (4'-$CH_2$—O-2') BNA; (B) β-D-Methyleneoxy (4'-$CH_2$—O-2') BNA; (C) Ethyleneoxy (4'-$(CH_2)_2$—O-2') BNA; (D) Aminooxy (4'-$CH_2$—O—N(R)-2') BNA; (E) Oxyamino (4'-$CH_2$—N(R)—O-2') BNA; (F) Methyl(methyleneoxy) (4'-$CH(CH_3)$—O-2') BNA (also referred to as constrained ethyl or cEt); (G) methylene-thio (4'-$CH_2$—S-2') BNA; (H) methylene-amino (4'-CH2-N(R)-2') BNA; (I) methyl carbocyclic (4'-$CH_2$—$CH(CH_3)$-2') BNA; (J) c-MOE (4'-$CH_2$—OMe-2') BNA and (K) propylene carbocyclic (4'-$(CH_2)_3$-2') BNA as depicted below.

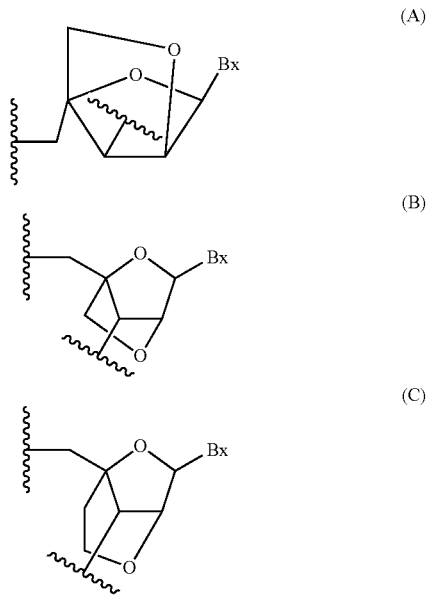

(D)
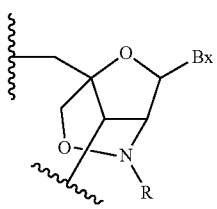

(E)
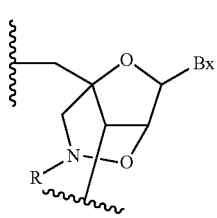

(F)
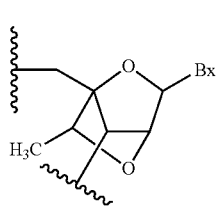

(G)
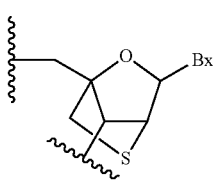

(H)
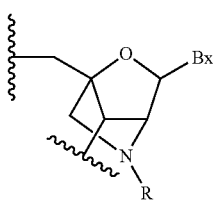

(I)
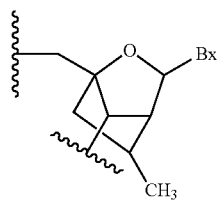

(J)
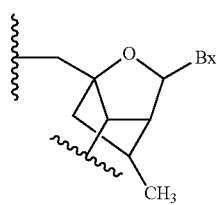

(K)
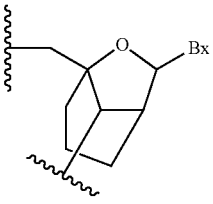

wherein Bx is a nucleobase moiety and R is, independently, H, a protecting group, or $C_1$-$C_{12}$ alkyl.

In certain embodiments, a 2'-modified nucleoside comprises a 2'-substituent group selected from F, $OCF_3$, $O-CH_3$, $OCH_2CH_2OCH_3$, 2'-$O(CH_2)_2SCH_3$, $O-(CH_2)_2-O-N(CH_3)_2$, $-O(CH_2)_2O(CH_2)_2N-(CH_3)_2$, and $O-CH_2-C(=O)-N(H)CH_3$.

In certain embodiments, a 2'-modified nucleoside comprises a 2'-substituent group selected from F, $O-CH_3$, and $OCH_2CH_2OCH_3$.

In certain embodiments, a sugar-modified nucleoside is a 4'-thio modified nucleoside. In certain embodiments, a sugar-modified nucleoside is a 4'-thio-2'-modified nucleoside. A 4'-thio modified nucleoside has a β-D-ribonucleoside where the 4' —O replaced with 4'-S. A 4'-thio-2'-modified nucleoside is a 4'-thio modified nucleoside having the 2' —OH replaced with a 2'-substituent group. Suitable 2'-substituent groups include 2' —$OCH_3$, 2' —$O-(CH_2)_2-OCH_3$, and 2' —F.

In certain embodiments, a modified oligonucleotide comprises one or more internucleoside modifications. In certain such embodiments, each internucleoside linkage of a modified oligonucleotide is a modified internucleoside linkage. In certain embodiments, a modified internucleoside linkage comprises a phosphorus atom.

In certain embodiments, a modified oligonucleotide comprises at least one phosphorothioate internucleoside linkage. In certain embodiments, each internucleoside linkage of a modified oligonucleotide is a phosphorothioate internucleoside linkage.

In certain embodiments, a modified oligonucleotide comprises one or more modified nucleobases. In certain embodiments, a modified nucleobase is selected from 5-hydroxymethyl cytosine, 7-deazaguanine and 7-deazaadenine. In certain embodiments, a modified nucleobase is selected from 7-deaza-adenine, 7-deazaguanosine, 2-aminopyridine and 2-pyridone. In certain embodiments, a modified nucleobase is selected from 5-substituted pyrimidines, 6-azapyrimidines and N-2, N-6 and O-6 substituted purines, including 2 aminopropyladenine, 5-propynyluracil and 5-propynylcytosine.

In certain embodiments, a modified nucleobase comprises a polycyclic heterocycle. In certain embodiments, a modified nucleobase comprises a tricyclic heterocycle. In certain embodiments, a modified nucleobase comprises a phenoxazine derivative. In certain embodiments, the phenoxazine can be further modified to form a nucleobase known in the art as a G-clamp.

In certain embodiments, a modified oligonucleotide is conjugated to one or more moieties which enhance the activity, cellular distribution or cellular uptake of the resulting antisense oligonucleotides. In certain such embodiments, the moiety is a cholesterol moiety. In certain embodiments, the moiety is a lipid moiety. Additional moieties for conjugation include carbohydrates, phospholipids, biotin, phenazine, folate, phenanthridine, anthraquinone, acridine, fluoresceins, rhodamines, coumarins, and dyes. In certain embodiments, the carbohydrate moiety is N-acetyl-D-galactosamine (GalNac). In certain embodiments, a conjugate group is attached directly to an oligonucleotide. In certain embodiments, a conjugate group is attached to a modified oligonucleotide by a linking moiety selected from amino, hydroxyl, carboxylic acid, thiol, unsaturations (e.g., double or triple bonds), 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted C1-C10 alkyl, substituted or unsubstituted C2-C10 alkenyl, and substituted or unsubstituted C2-C10 alkynyl. In certain such embodiments, a substituent group is selected from hydroxyl, amino, alkoxy, carboxy, benzyl, phenyl, nitro, thiol, thioalkoxy, halogen, alkyl, aryl, alkenyl and alkynyl.

In certain such embodiments, the compound comprises a modified oligonucleotide having one or more stabilizing groups that are attached to one or both termini of a modified oligonucleotide to enhance properties such as, for example, nuclease stability. Included in stabilizing groups are cap structures. These terminal modifications protect a modified oligonucleotide from exonuclease degradation, and can help in delivery and/or localization within a cell. The cap can be present at the 5'-terminus (5'-cap), or at the 3'-terminus (3'-cap), or can be present on both termini. Cap structures include, for example, inverted deoxy abasic caps.

Certain Pharmaceutical Compositions

Provided herein are pharmaceutical compositions comprising oligonucleotides. In certain embodiments, a pharmaceutical composition provided herein comprises a compound comprising a modified oligonucleotide consisting of 15 to 25 linked nucleosides and having a nucleobase sequence complementary to miR-21. In certain embodiments, a pharmaceutical composition provided herein comprises a compound consisting of a modified oligonucleotide consisting of 8 to 30 linked nucleosides and having a nucleobase sequence complementary to miR-21. In certain embodiments, a pharmaceutical composition provided herein comprises a compound comprising a modified oligonucleotide consisting of 12 to 25 linked nucleosides and having a nucleobase sequence complementary to miR-21.

Suitable administration routes include, but are not limited to, oral, rectal, transmucosal, intestinal, enteral, topical, suppository, through inhalation, intrathecal, intracardiac, intraventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the kidney).

In certain embodiments, a pharmaceutical composition is administered in the form of a dosage unit (e.g., tablet, capsule, bolus, etc.). In some embodiments, a pharmaceutical compositions comprises a modified oligonucleotide at a dose within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of an oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide. Further, in some embodiments, the lyophilized modified oligonucleotide is an amount of an oligonucleotide within a range selected from 25 mg to 800 mg, 25 mg to 700 mg, 25 mg to 600 mg, 25 mg to 500 mg, 25 mg to 400 mg, 25 mg to 300 mg, 25 mg to 200 mg, 25 mg to 100 mg, 100 mg to 800 mg, 200 mg to 800 mg, 300 mg to 800 mg, 400 mg to 800 mg, 500 mg to 800 mg, 600 mg to 800 mg, 100 mg to 700 mg, 150 mg to 650 mg, 200 mg to 600 mg, 250 mg to 550 mg, 300 mg to 500 mg, 300 mg to 400 mg, and 400 mg to 600 mg. The lyophilized drug product may be packaged in a 2 mL Type I, clear glass vial (ammonium sulfate-treated), stoppered with a bromobutyl rubber closure and sealed with an aluminum FLIP-OFF® overseal.

In certain embodiments, the pharmaceutical compositions provided herein may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide(s) of the formulation.

Lipid moieties have been used in nucleic acid therapies in a variety of methods. In one method, the nucleic acid is introduced into preformed liposomes or lipoplexes made of mixtures of cationic lipids and neutral lipids. In another method, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid. In certain embodiments, such preparations comprise one or more compounds each individually having a structure defined by formula (Z) or a pharmaceutically acceptable salt thereof,

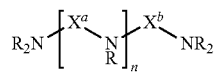

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (Z) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein is prepared using known techniques, including, but not limited to mixing, dissolving, granulating, dragee-making, levigating, emulsifying, encapsulating, entrapping or tableting processes.

In certain embodiments, a pharmaceutical composition provided herein is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition provided herein is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition provided herein is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition provided herein comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Certain Additional Therapies

Treatments for a disease associated with miR-21 may comprise more than one therapy. As such, in certain embodiments provided herein are methods for treating a subject having or suspected of having a disease associated with miR-21 comprising administering at least one therapy in addition to administering a modified oligonucleotide having a nucleobase sequence complementary to the microRNA.

In certain embodiments, the at least one additional therapy comprises a pharmaceutical agent.

In certain embodiments, pharmaceutical agents include anti-inflammatory agents. In certain embodiments, an anti-inflammatory agent is a steroidal anti-inflammatory agent. In certain embodiments, a steroid anti-inflammatory agent is a corticosteroid. In certain embodiments, a corticosteroid is prednisone. In certain embodiments, an anti-inflammatory agent is a non-steroidal anti-inflammatory drugs. In certain embodiments, a non-steroidal anti-inflammatory agent is ibuprofen, a COX-I inhibitors, or a COX-2 inhibitors.

In certain embodiments, pharmaceutical agents include anti-diabetic agents. Antidiabetic agents include, but are not limited to, biguanides, glucosidase inhibitors, insulins, sulfonylureas, and thiazolidenediones.

In certain embodiments, pharmaceutical agents include, but are not limited to, diuretics (e.g. sprionolactone, eplerenone, furosemide), inotropes (e.g. dobutamine, milrinone), digoxin, vasodilators, angiotensin II converting enzyme (ACE) inhibitors (e.g. are captopril, enalapril, lisinopril, benazepril, quinapril, fosinopril, and ramipril), angiotensin II receptor blockers (ARB) (e.g. candesartan, irbesartan, olmesartan, losartan, valsartan, telmisartan, eprosartan), calcium channel blockers, isosorbide dinitrate, hydralazine, nitrates (e.g. isosorbide mononitrate, isosorbide dinitrate), hydralazine, beta-blockers (e.g. carvedilol, metoprolol), and natriuretic peptides (e.g. nesiritide). In certain embodiments, an ACE inhibitor is selected from cilazapril, perindopril, and trandolapril.

In certain embodiments, an ACE inhibitor is administered at a dose of 0.025 to 0.1 mg/kg body weight. In certain embodiments, an ACE inhibitor is administered at a dose of 0.125 to 1.0 mg/kg bodyweight. In certain embodiments, an ACE inhibitor is administered at a dose ranging from 1 to 6 mg/m$^2$/day. In certain embodiments, an ACE inhibitor is administered at a dose ranging from 1 to 2 mg/m$^2$/day. In certain embodiments, an ACE inhibitor is administered at a dose ranging from 2 to 4 mg/m$^2$/day. In certain embodiments, an ACE inhibitor is administered at a dose ranging from 0.5 to 1 mg/m$^2$/day.

In certain embodiment, ramipril is administered at a dose ranging from 1 to 6 mg/m$^2$/day. In certain embodiments, ramipril is administered at a dose ranging from 1 to 2 mg/m$^2$/day. In certain embodiment, enalapril is administered at a dose ranging from 2 to 4 mg/m$^2$/day. In certain embodiment, lisinopril is administered at a dose ranging from 4 to 8 mg/m$^2$/day. In certain embodiment, benazepril is administered at a dose ranging from 4 to 8 mg/m$^2$/day. In certain embodiment, fosinopril is administered at a dose ranging from 4 to 8 mg/m$^2$/day. In certain embodiment, quinapril is administered at a dose ranging from 4 to 8 mg/m$^2$/day. In certain embodiment, cilazapril is administered at a dose ranging from 1 to 2 mg/m$^2$/day. In certain embodiment, perinpril is administered at a dose ranging from 1 to 2 mg/m$^2$/day. In certain embodiment, trandolapril is administered at a dose ranging from 0.5 to 1 mg/m$^2$/day.

In certain embodiments, an ARB is administered at a dose ranging from 6.25 to 150 mg/m2/day. In certain embodiments, an ARB is administered at a dose of 6.25 mg/m$^2$/day. In certain embodiments, an ARB is administered at a dose of 10 mg/m$^2$/day. In certain embodiments, an ARB is administered at a dose of 12.5 mg/m$^2$/day. In certain embodiments, an ARB is administered at a dose of 18.75 mg/m$^2$/day. In certain embodiments, an ARB is administered at a dose of 37.5 mg/m$^2$/day. In certain embodiments, an ARB is administered at a dose of 50 mg/m$^2$/day. In certain embodiments, an ARB is administered at a dose of 150 mg/m$^2$/day.

In certain embodiments, losartan is administered at a dose of 12.5 mg/m$^2$/day. In certain embodiments, losartan is administered at a dose of 12.5 mg/m$^2$/day. In certain embodiments, candesartan is administered at a dose of 6.25 mg/m$^2$/day. In certain embodiments, irbestartan is administered at a dose of 37.5 mg/m$^2$/day. In certain embodiments, telmisartan is administered at a dose of 10 mg/m$^2$/day. In certain embodiments, valsartan is administered at a dose of 18.75 mg/m$^2$/day. In certain embodiments, espresartan is administered at a dose of 150 mg/m$^2$/day.

In certain embodiments, a pharmaceutical agent is an aldosterone antagonsist. In certain embodiments, an aldosterone antagonist is spironolactone. In certain embodiments, spironolactone is administered at a dose ranging from 10 to 35 mg daily. In certain embodiments, spironolactone is administered at a dose of 25 mg daily.

In certain embodiments, pharmaceutical agents include heparinoids. In certain embodiments, a heparinoid is pentosan polysulfate.

In certain embodiments, a pharmaceutical agent is a pharmaceutical agent that blocks one or more responses to fibrogenic signals.

In certain embodiments, a pharmaceutical agent is an anti-connective tissue growth factor therapy. In certain embodiments, an anti-CTGF therapy is a monoclonal antibody against CTGF.

In certain embodiments, an additional therapy may be a pharmaceutical agent that enhances the body's immune system, including low-dose cyclophosphamide, thymostimulin, vitamins and nutritional supplements (e.g., antioxidants, including vitamins A, C, E, beta-carotene, zinc, selenium, glutathione, coenzyme Q-10 and echinacea), and vaccines, e.g., the immunostimulating complex (ISCOM), which comprises a vaccine formulation that combines a multimeric presentation of antigen and an adjuvant.

In certain embodiments, the additional therapy is selected to treat or ameliorate a side effect of one or more pharmaceutical compositions of the present invention. Such side effects include, without limitation, injection site reactions, liver function test abnormalities, kidney function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

Further examples of additional pharmaceutical agents include, but are not limited to, immunoglobulins, including, but not limited to intravenous immunoglobulin (IVIg); analgesics (e.g., acetaminophen); salicylates; antibiotics; antivirals; antifungal agents; adrenergic modifiers; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Kits

The present invention also provides kits. In some embodiments, the kits comprise one or more compounds of the invention comprising a modified oligonucleotide, wherein the nucleobase sequence of the oligonucleotide is complementary to the nucleobase sequence of miR-21. The compounds complementary to miR-21 can have any of the nucleoside patterns described herein. In some embodiments, the compounds complementary to miR-21 can be present within a vial. A plurality of vials, such as 10, can be present in, for example, dispensing packs. In some embodiments, the vial is manufactured so as to be accessible with a syringe. The kit can also contain instructions for using the compounds complementary to miR-21.

In some embodiments, the kits may be used for administration of the compound complementary to miR-21 to a subject. In such instances, in addition to compounds complementary to miR-21, the kit can further comprise one or more of the following: syringe, alcohol swab, cotton ball, and/or gauze pad. In some embodiments, the compounds complementary to miR-21 can be present in a pre-filled syringe (such as a single-dose syringes with, for example, a 27 gauge, ½ inch needle with a needle guard), rather than in a vial. A plurality of pre-filled syringes, such as 10, can be present in, for example, dispensing packs. The kit can also contain instructions for administering the compounds complementary to miR-21.

Certain Experimental Models

In certain embodiments, the present invention provides methods of using and/or testing modified oligonucleotides of the present invention in an experimental model. Those having skill in the art are able to select and modify the protocols for such experimental models to evaluate a pharmaceutical agent of the invention.

Generally, modified oligonucleotides are first tested in cultured cells. Suitable cell types include those that are related to the cell type to which delivery of a modified oligonucleotide is desired in vivo. For example, suitable cell types for the study of the methods described herein include primary or cultured cells.

In certain embodiments, the extent to which a modified oligonucleotide interferes with the activity of miR-21 is assessed in cultured cells. In certain embodiments, inhibition of microRNA activity may be assessed by measuring the levels of the microRNA. Alternatively, the level of a predicted or validated microRNA-regulated transcript may be measured. An inhibition of microRNA activity may result in the increase in the miR-21-regulated transcript, and/or the protein encoded by miR-21-regulated transcript. Further, in certain embodiments, certain phenotypic outcomes may be measured.

Several animal models are available to the skilled artisan for the study of miR-21 in models of human disease. For example, inhibitors of miR-21 may be studied in an experimental model of Alport Syndrome, for example Col4a3 knockout mice (Col4a3$^{-/-}$ mice). The severity of the disease in the mouse model depends upon the genetic background of the mouse carrying the Col4a3 mutation. For example, the onset and progression of the disease are generally more rapid on the 129X1/SvJ relative to the C57BL/6J background. Accordingly, the genetic background of the Col4a3$^{-/-}$ mouse may be selected to vary the onset and progression of disease. Additional models include canine models of X-linked, autosomal recessive or autosomal dominant Alport Syndrome. See, for example, Kashtan, *Nephrol. Dial. Transplant,* 2002, 17: 1359-1361.

Certain Quantitation Assays

The effects of antisense inhibition of miR-21 following the administration of modified oligonucleotides may be assessed by a variety of methods known in the art. In certain embodiments, these methods are be used to quantitate microRNA levels in cells or tissues in vitro or in vivo. In certain embodiments, changes in microRNA levels are measured by microarray analysis. In certain embodiments, changes in microRNA levels are measured by one of several commercially available PCR assays, such as the TaqMan® MicroRNA Assay (Applied Biosystems). In certain embodiments, antisense inhibition of miR-21 is assessed by measuring the mRNA and/or protein level of a target of miR-21. Antisense inhibition of miR-21 generally results in the increase in the level of mRNA and/or protein of a target of the microRNA.

Target Engagement Assay

Modulation of microRNA activity with an anti-miR or microRNA mimic may be assessed by measuring target engagement. In certain embodiments, target engagement is measured by microarray profiling of mRNAs. The sequences of the mRNAs that are modulated (either increased or decreased) by the anti-miR or microRNA mimic are searched for microRNA seed sequences, to compare modulation of mRNAs that are targets of the microRNA to modulation of mRNAs that are not targets of the microRNA. In this manner, the interaction of the anti-miR with miR-21, or miR-21 mimic with its targets, can be evaluated. In the case of an anti-miR, mRNAs whose expression levels are increased are screened for the mRNA sequences that comprise a seed match to the microRNA to which the anti-miR is complementary.

EXAMPLES

The following examples are presented in order to more fully illustrate some embodiments of the invention. They should in no way be construed, however, as limiting the broad scope of the invention. Those of ordinary skill in the art will readily adopt the underlying principles of this discovery to design various compounds without departing from the spirit of the current invention.

Example 1

Anti-miR-21 in a Model of Alport Syndrome

Col4a3$^{-/-}$ mice on the 129sv genetic background spontaneously develop severe kidney disease similar to human Alport Syndrome. As such, Col4a3$^{-/-}$ mice are used as an experimental model of Alport Syndrome.

Modified oligonucleotides complementary to miR-21 (anti-miR-21 compounds) were tested in the Col4a3$^{-/-}$ model of Alport Syndrome. Wild-type mice were used as control mice.

The structure of the anti-miR-21 compound is 5'-A$_E$C$_S$ATC$_S$AGTC$_S$TGAU$_S$AAGC$_S$TA$_E$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides. Each internucleoside linkage is a phosphorothioate internucleoside linkage.

At 3 weeks of age, mice were genotyped to identify Col4a3−/− mice. From 3 weeks of age to 9 weeks of age, sex-matched littermates of mice were treated with anti-miR-21 or PBS. Anti-miR-21 was administered subcutaneously at a dose of 25 mg/kg, twice per week. Treatment groups were: (1) wild-type mice, PBS administration, n=8; (2) Col4a3−/− mice, PBS administration, n=12; (3) Col4a3−/− mice, anti-miR-21 administration, n=12. Wild type littermates of Col4a3−/− mice were used as the wild-type control mice. An overnight urine sample (approximately 16 hours) was collected weekly. Plasma and kidneys were harvested at the end of week 9. Fluid and tissue samples were analyzed to determine changes in kidney function, kidney damage and glomerular sclerosis and interstitial fibrosis.

Endpoints in blood or urine included measurement of blood urea nitrogen (BUN), albuminuria, albumin/creatinine ratio, glomerular filtration rate. Histological analysis included evaluation of glomerular sclerosis, interstitial fibrosis, injury to the tubules, macrophage infiltration, and presence of myofibroblasts.

Blood urea nitrogen (BUN) was measured at week 9. Statistical significance was calculated by the Mann Whitney test. As shown in FIG. 1A, a statistically significant reduction in BUN was observed in animals treated with anti-miR-21, relative to PBS-treated control animals at the end of the study. The reduced BUN was observed overall (FIG. 1A), as well as in male mice only (approximately 90 mg/dL compared to approximately 25 mg/dL in control male mice) and female mice only (approximately 70 mg/dL compared to approximately 25 mg/dL in control female mice) not shown). The BUN in Col4a3+/+ mice was approximately 12.5 mg/kL (within normal limits; not shown). BUN is a blood marker of kidney function. Higher BUN correlates with poorer kidney function. A reduction in BUN is an indicator of reduced kidney injury and damage and improved function.

Figure 1B:
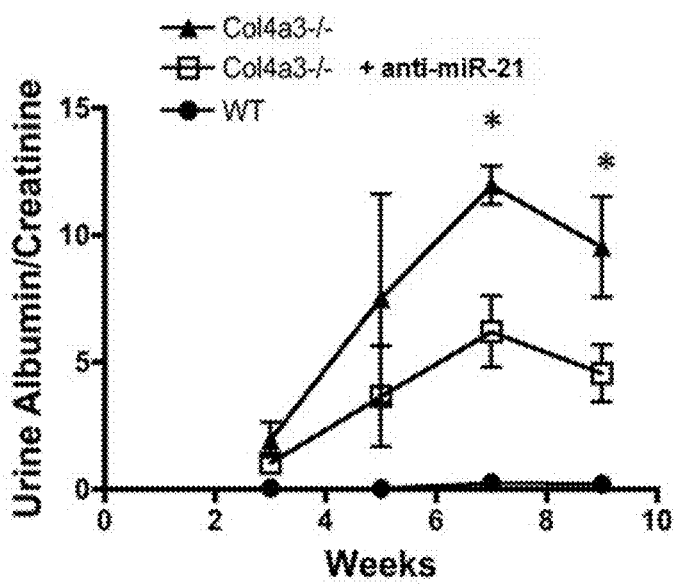

Albuminuria was assessed by measuring albumin in urine samples, collected over 16 hours at a frequency of once weekly, by ELISA and by normalizing to urinary creatinine excretion. All analyses were performed at the same time at the end of the study. As shown in FIG. 1B, Col4a3−/− mice develop severe albuminuria. However, mice treated with anti-miR-21 developed much less albuminuria as detected by a reduction in urinary albumin to creatinine ratio. This reduction was observed by week 7 and persisted to week 9. Wild type littermates of Col4a3−/− mice exhibited no albuminuria, as expected. Albuminuria is a sensitive measure of glomerular and tubular damage. A reduction in albumin to creatinine ratio indicates a reduction in glomerular and/or tubular disease.

Figure 2:
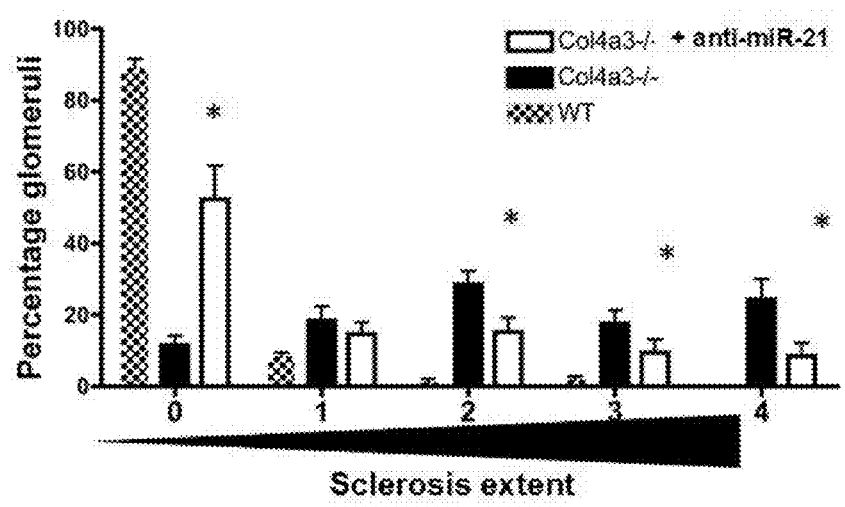
FIG. 2. Anti-miR-21 prevents glomerulosclerosis in Col4a3−/− mice. Glomerulosclerosis was evaluated using semi-quantitative sclerosis scores ranging from 0 (no sclerosis) to 4 (complete sclerosis) (n=10).
Figure 3A:
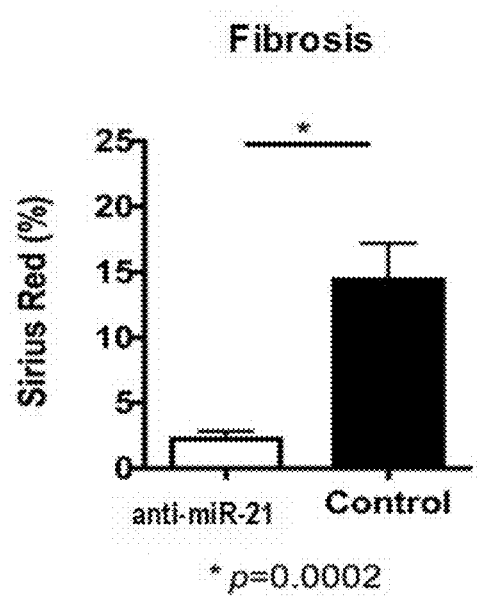
FIG. 3A-B. Anti-miR-21 reduces fibrosis in Col4a3−/− mice. (A) Quantification of Picrosirius (Sirius) red-stained fibrosis in kidney (n=6) and (B) Quantitative PCR of Col1a1 transcripts normalized to GAPDH (n=6). * indicates statistical significance.
Figure 3B:
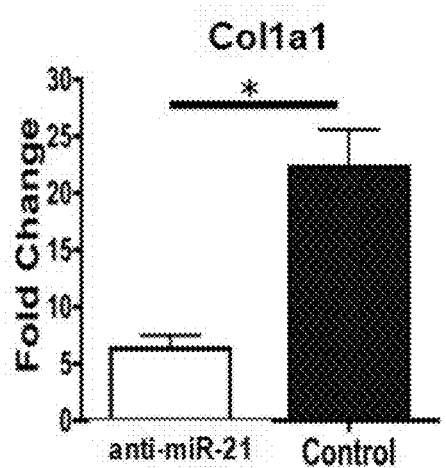

Alport Syndrome is also characterized by progressive development of glomerulosclerosis and significant interstitial kidney fibrosis that occurs as inappropriate glomerular leakage occurs. Accordingly, glomerulosclerosis was assessed by blinded scoring of glomeruli for sclerotic lesions (loss of capillary loop+fibrosis or hyalinosis). Thirty glomeruli were scored sequentially from each mouse by a blinded observer. The score was from 0-4 where 0=normal; 1=<25% of the glomerulus affected by sclerosis; 2=25-50% of the glomerulus is affected by sclerosis; 3=50-75% of the glomerulus is affected by sclerosis; 4=75-100% of the glomerulus is affected by sclerosis. The proportion of glomeruli with no disease was much higher in mice treated with anti-miR-21 and the proportion of glomeruli with moderately or severely affected glomeruli (score 2-4) was significantly higher in the mice treated with the PBS (FIG. 2). Glomeruli were also scored in wild type littermates (WT) of Col43a−/− mice. Interstitial fibrosis was measured morphometrically in whole sagittal sections stained with Picrosirius red from PBS-treated and anti-miR-21 Col4a3−/− animals. As shown in FIG. 3A, a statistically significant reduction in interstitial fibrosis was observed in the anti-miR-21 treated Col4a3−/− mice. In addition, quantitative PCR for the transcripts for the major pathological matrix protein Collagen Iα(1) (Col1a1) showed that the kidney tissue from anti-miR-21 treated Col4a3−/−mice showed much less production of this pathological collagen (FIG. 3B).

Figure 4A:
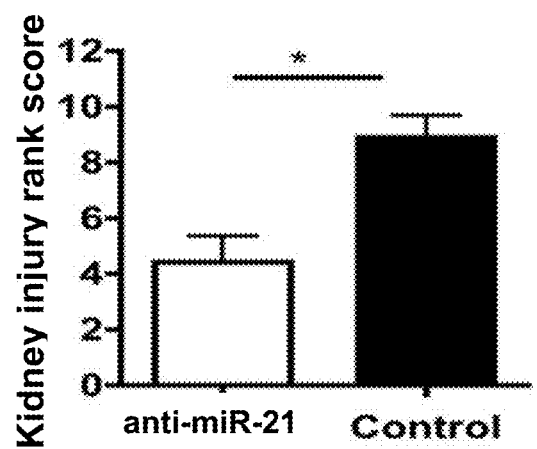
FIG. 4A-C. Anti-miR-21 reduces kidney injury ranking in Col4a3−/− mice. (A) Kidney injury rank score of renal sections of 9 week old mice. (B) Proportion of glomerular crescents (n=5). (C) Quantification of tubule injury (n=5). * indicates statistical significance.
Figure 4B:
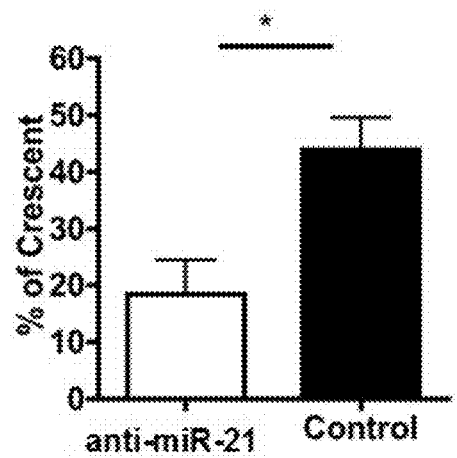
Figure 4C:
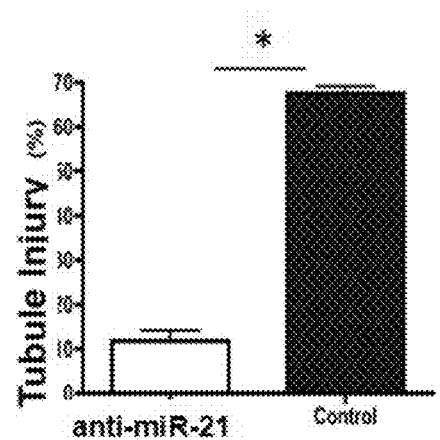

Renal tissue injury was assessed in paraffin-embedded and paraformaldehyde (4%)-fixed tissue sections stained by the periodic acid-Schiff (PAS) reaction. Initially the kidney sections were ranked for overall injury based on tubule and glomerular injury and inflammation. Damage was assessed based on a variety of factors including tubule dilation, loss of brush border, cellular infiltration, glomerular inflammation, interstitial edema and cellular necrosis. Kidney sections were ranked in a blinded fashion for overall injury and given a kidney injury rank score. The kidney sections from Col4a3−/− mice showed a significantly lower kidney injury rank score, which is indicative of less kidney injury (FIG. 4A). To analyze this in more detail, the glomeruli were assessed by a blinded observer for the proportion that had glomerular crescents. The crescent is a proliferation of cells within Bowman's capsule, is defined by ≥2 layers of cells within Bowman's space. The crescent is a well-established marker of glomerular injury. In Col4a3−/− mice that received anti-miR-21 the proportion of glomeruli with crescents was approximately 44%, whereas in mice that received the PBS control treatment, the proportion of glomeruli with crescents was approximately 19% (FIG. 4B). In Col4a3+/+ littermates, the proportion of glomeruli with crescents was less than 5% (not shown). The tubules of the nephrons of the kidney are also a site for damage. The tubule damage was assessed by overlaying a grid over sequential images covering the whole sagittal section of each kidney. In a blinded fashion, damage of the tubules was assessed in each square of the grid. Tubular damage was assessed based on the presence of tubule dilation/flattening, loss of brush border, cellular infiltration, and cellular necrosis. The presence of these features results in a positive score for that square on the grid. An overall score is applied to each image which is the % of squares that has tubule damage. This is averaged for all the images from that kidney. The average score for each kidney is then subjected to statistical analysis. As is shown, the tubule injury score was significantly lower in the Col4a3−/− mice treated with anti-miR-21, relative to the Col4a3−/− receiving PBS (FIG. 4C). The tubule injury score in Col4a3+/+ littermates was less than 10% (not shown).

Figure 5A:
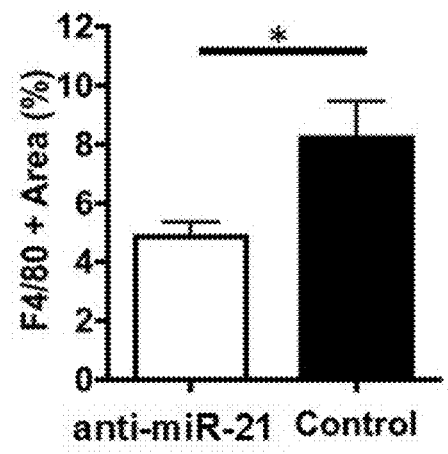
FIG. 5A-B Anti-miR-21 reduces macrophage infiltration (A) and decreases myofibroblasts (B) in Col4a3−/− mice. (A) Quantification of F4/80 stain of renal sections of 9 week old mice (n=5). (B) Quantification of αSMA stain of renal sections of 9 week old mice (n=5). * indicates statistical significance.
Figure 5B:
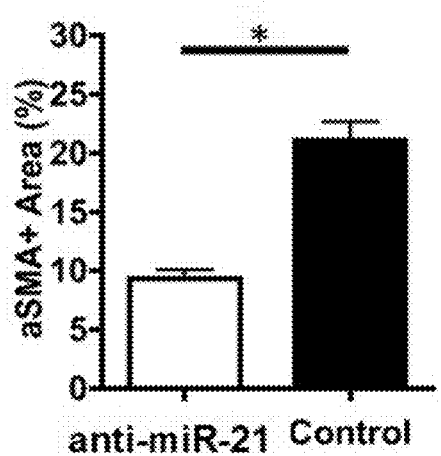

Additional histological analysis of kidney samples was performed to evaluate macrophage infiltration, endothelial stability, and the myofibroblast deposition. As judged by F4/80 staining, macrophage infiltration was reduced in anti-miR-21 treated Col4a3−/− mice compared to PBS-treated Col4a3−/− control mice (FIG. 5A). Immunocytochemical staining for CD31 demonstrated an improvement in endothelial stability in anti-miR-21 treated Col4a3−/− mice compared to PBS-treated Col4a3−/− control mice (not shown). Detection of alpha-SMA revealed a reduction in myofibroblast deposition in anti-miR-21 treated Col4a3−/− mice compared to PBS-treated Col4a3−/− control mice (FIG. 5B). In Col4a3+/+ mice, alpha-SMA staining was approximately 5% (not shown).

Figure 6A:
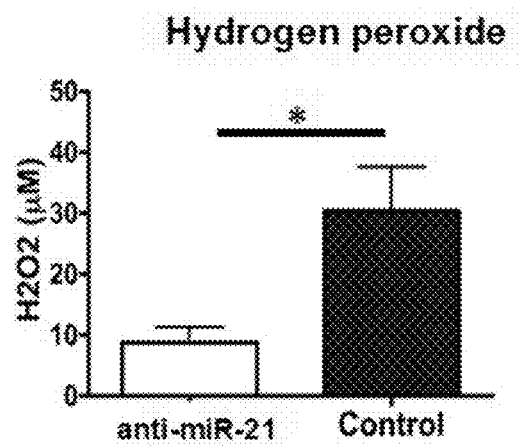
FIG. 6A-B. Anti-miR-21 reduces reactive oxygen species in Col4a3−/− mice. (A) Quantification of hydrogen peroxide in urine of Col4a3−/− mice treated with anti-miR-21 or PBS control (n=8; * indicates statistical significance); (B) Quantification of DES in kidney tissue of Col4a3−/− mice treated with anti-miR-21 or PBS control, and in wild type mice (n=3 per group; * indicates statistical significance).
Figure 6B:
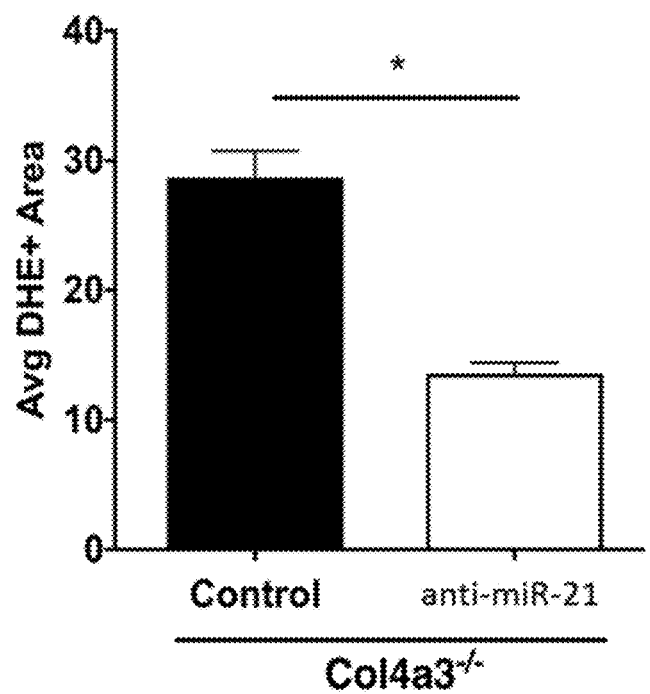

Reactive oxygen species (ROS) are a byproduct of normal cellular metabolism. During cellular stress, excess ROS can cause lipid peroxidation of cell and organelle membranes, resulting in disruption of the structural integrity and capacity for cell transport and energy production. In the kidney, ROS produced during cellular stress can cause renal injury. To assess whether the generation of ROS was reduced following inhibition of miR-21 in Col4a3−/− mice, urinary hydrogen peroxide levels were measured in anti-miR-21 and PBS-treated mice. Urinary hydrogen peroxide levels were significantly reduced in mice that received anti-miR-21 (FIG. 6A). In Col4a3+/+ mice, urinary hydrogen peroxide levels were less than 5 μM (not shown). Further, immunocytochemical staining of kidney tissue with dihydroethidium (DHE), which is a measure of ROS, demonstrated a reduction in ROS in the kidney tissue of anti-miR-21 treated Col4a3−/− mice compared to PBS-treated control mice (FIG. 6B). In Col4a3+/+ mice, less than 10% DHE staining was observed (not shown). These data demonstrate reduction of ROS in both the urine and kidney tissue in Col4a3−/− mice treated with anti-miR-21. Accordingly, one mechanism by which anti-miR-21 may reduce kidney injury may include a reduction in the generation of reactive oxygen species.

Immunoblotting of protein in the kidneys of Col4a3−/− mice treated with anti-miR-21 revealed an increase in the amount of MPV17L protein in the kidney, relative to Col4a3−/− mice. MPV17L is a mitochondrial inner membrane protein that is implicated in the metabolism of reactive oxygen species, and protects against oxidative stress. Accordingly, the reduced generation of ROS following anti-miR-21 treatment may occur at least in part due to increased MPV17L levels. To further explore the mechanistic effects of anti-miR-21, PPAR-alpha protein was measured by immunoblotting of the kidneys of Col4a3−/− mice treated with PBS or anti-miR-21 treatment. Anti-miR-21 treatment increased PPAR-alpha protein, suggesting a stimulation of metabolic pathways.

Figure 7:
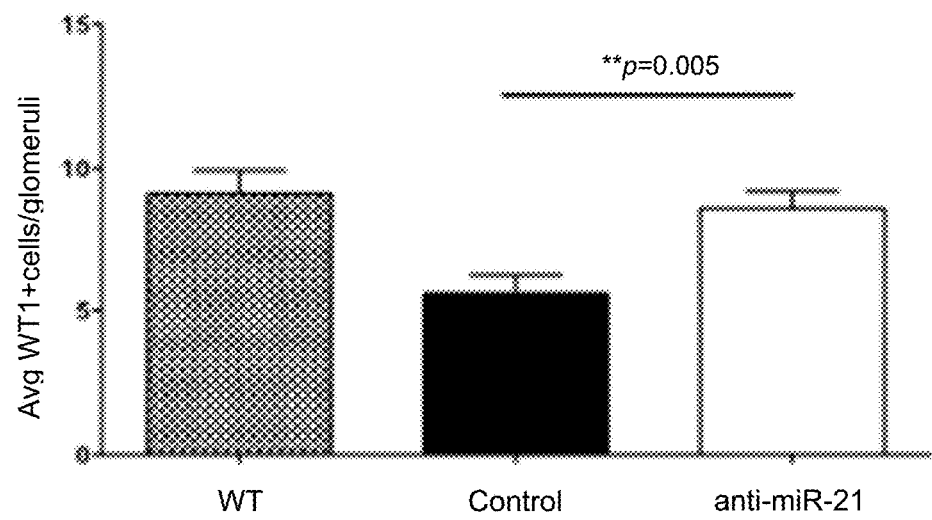
FIG. 7. Anti-miR-21 improves podocyte number in Col4a3−/− mice. Quantification of number of WT1-positive cells in the glomerulus of Col4a3−/− mice treated with anti-miR-21 or PBS control (n=3; p=0.005).

Podocytes are highly specialized epithelial cells that are an essential component of the glomerular filtration barrier. Podocyte loss can lead to proteinuria, and in some disease states to glomerularsclerosis. To evaluate whether podocyte number was affected by inhibition of miR-21 in Col4a3−/− mice, podocyte number was measured in anti-miR-21 and PBS-treated mice. Podocyte number was significantly increased in Col4a3−/− mice that received anti-miR-21, relative to PBS-treated mice, and was comparable to the podocyte number observed in wild type littermates of Col4a3−/− mice (FIG. 7). Accordingly, one mechanism by which anti-miR-21 may reduce kidney injury in a model of Alport Syndrome is by preventing or reducing podocyte loss.

A similar study was conducted using the following anti-miR-21 compounds:

```
anti-miR-21 compound #1 (above):
                                        (SEQ ID NO: 3)
5'-A_EC_SATC_SAGTC_STGAU_SAAGC_STA_E-3' anti-miR-21 compound #2:
                                        (SEQ ID NO: 3)
5'-A_EC_SATC_SA_SGTC_SU_SGAU_SA_SAGC_SUsA_E-3';

anti-miR-21 compound #3:
                                        (SEQ ID NO: 4)
5'-^MeC_EA_SA_ST_EC_SU_SA_EA_EU_SA_SA_EG_EC_ST_EA_S-3';
and anti-miR-21 compound #4:
                                        (SEQ ID NO: 3)
5'-A_EC_SA_ET_EC_SA_EG_ET_EC_STGAU_SAAGC_SU_SA_S-3';
``` where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides; and a superscript "Me" indicates a 5-methyl group on the base of the nucleoside. Each internucleoside linkage is a phosphorothioate internucleoside linkage.

Each compound was administered to three-week old Col4a3−/−mice at a dose of 25 mg/kg, twice weekly, for nine weeks. Control groups included Col4a3−/− mice treated with PBS, and wild-type littermates of Col4a3−/− mice. Each treatment group contained 10 to 12 mice. For compounds #1, 2, and 4, endpoints were evaluated as described above and included BUN, urinary albumin to creatinine ratio, kidney injury (PAS staining), glomerulosclerosis, and proportion of glomeruli with crescents. For compound #3, endpoints included BUN, urinary albumin to creatinine ratio, and collagen gene expression (as a measure of fibrosis), evaluated as described above.

Consistent with the results described above, anti-miR-21 compound #1 improved all endpoints evaluated. The efficacy of both anti-miR-21 compounds #2 was similar to that of compound #1, with improvements observed in BUN, urinary albumin to creatinine ratio, kidney injury, extent of glomerulosclerosis, and percentage of glomeruli with crescents. The efficacy of compound #3 was similar to that of compound #1, with improvements in BUN, urinary albumin to creatinine ratio, and Col1a1 expression. Anti-miR-21 compound #4, while less efficacious than compounds the other compounds tested, still resulted in improvements in BUN, kidney injury, extent of glomerulosclerosis, and percentage of glomeruli with crescents.

Taken together, these data illustrate that in a model of Alport Syndrome, anti-miR-21 treatment attenuated the loss of kidney function and development of albuminuria. Glomerulosclerosis and interstitial fibrosis were markedly attenuated and proximal tubules were preserved. As anti-miR-21 prevents progressive loss of kidney function in the Col4a3−/− mouse, and attenuates both glomerular and tubulo-interstitial disease, anti-miR-21 is a therapeutic agent for human Alport Syndrome.

Example 2

Elevation of miR-21 in a Model of Alport Syndrome

To evaluate the dysregulation of miR-21 in an experimental model of Alport Syndrome, miR-21 levels were measured in kidney tissue harvested from mice. RNA was isolated from whole kidney and miR-21 was measured by quantitative PCR. In Col4a3−/− mice, miR-21 levels were elevated approximately three-fold relative to miR-21 levels in wild-type mice.

Accordingly, a subject receiving treatment for Alport Syndrome may be identified as having elevated miR-21 in kidney biopsy material, urine, or blood, prior to administration of the treatment.

Example 3

Survival Studies in a Model of Alport Syndrome

Wild-type mice generally live for 2 to 3 years (or 730 to 1095 days). In Col4a3−/− mice on a 129X1/SvJ background, end-stage renal failure can occur as early as 2 months of age. In Col4a3−/− on a C57BL/6J background, end-stage renal failure can occur as early as 6 months of age. Regardless of the background, the lifespan of Col4a3−/− mice is significantly shorter than that of wild-type mice. As such, Col4a3−/− mice, on any genetic background, can be serve as a model for end-stage renal failure in Alport Syndrome and can be used to evaluate the effects of candidate therapeutic agents on life expectancy.

Mice are genotyped to identify Col4a3−/− mice. Anti-miR-21 is administered subcutaneously at a dose of ranging from 10 to 25 mg/kg, once or twice per week for up to one year. PBS may be administered as a control treatment. Overnight urine samples (approximately 16 hours) are collected on a weekly or monthly schedule throughout the study. Age of each mouse at death is recorded. Plasma and kidneys are collected at death or at the end of the study. Fluid and tissue samples are analyzed to determine changes in kidney function, glomerularsclerosis, and fibrosis.

Fluid and tissue samples are analyzed to determine changes in kidney function, kidney damage and glomerular sclerosis and interstitial fibrosis. Endpoints in blood or urine include measurement of blood urea nitrogen (BUN), albuminuria, albumin/creatinine ratio, glomerular filtration rate. Histological analysis includes evaluation of glomerular sclerosis, interstitial fibrosis, injury to the tubules, macrophage infiltration, and presence of myofibroblasts.

Delay in the onset of end-stage renal failure and increased life expectancy in anti-miR-21 treated mice, relative to PBS-treated control mice, is observed, suggesting that anti-miR-21 is a therapeutic agent that can increase the life expectancy of subjects with Alport Syndrome.

Anti-miR-21Increases Survival in a Model of Alport Syndrome-single Dose Study

To evaluate the effects of anti-miR-21 on survival in an experimental model of Alport Syndrome, anti-miR-21 compound was administered to Col4a3−/− mice.

The structure of the anti-miR-21 compound is 5'-$A_E C_S ATC_S AGTC_S TGAU_S AAGC_S TA_E$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides. Each internucleoside linkage is a phosphorothioate internucleoside linkage.

Col4a3+/1 mice (heterozygotes) on a 129X1/SvJ background were crossed to generate Col4a3−/− mice. At 3 weeks of age, mice were genotyped to identify Col4a3−/− mice. Treatment groups were: (1) Col4a3+/+ mice (wild-type littermates), PBS administration, twice weekly, n=12; (2) Col4a3−/− mice, PBS administration, twice weekly, n=12; (3) Col4a3−/− mice, 25 mg/kg anti-miR-21 administration subcutaneously, twice weekly, n=12. Treatments were administered twice weekly, from week 3 through week 16. Animal weights were measured weekly, and lifespan was recorded.

Figure 8A:
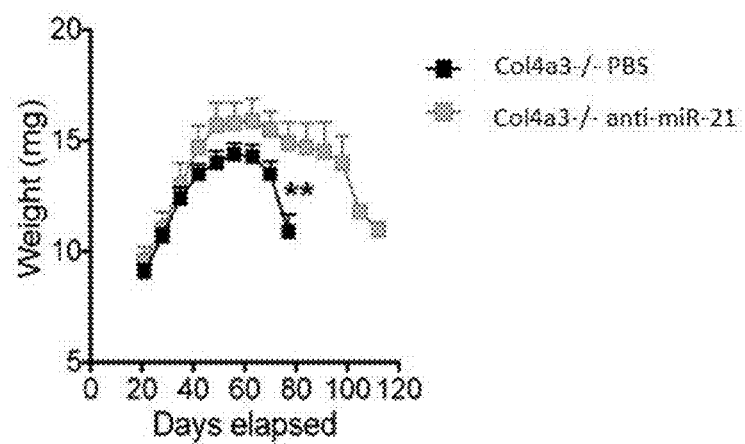
FIG. 8A-B. Anti-miR-21 increases lifespan of Col4a3−/− mice. (A) Weight of Col4a3−/− mice treated with anti-miR-21 or PBS control (p<0.01); (B) Lifespan of Col4a3−/− mice treated with anti-miR-21 or PBS control (p<0.001).
Figure 8B:
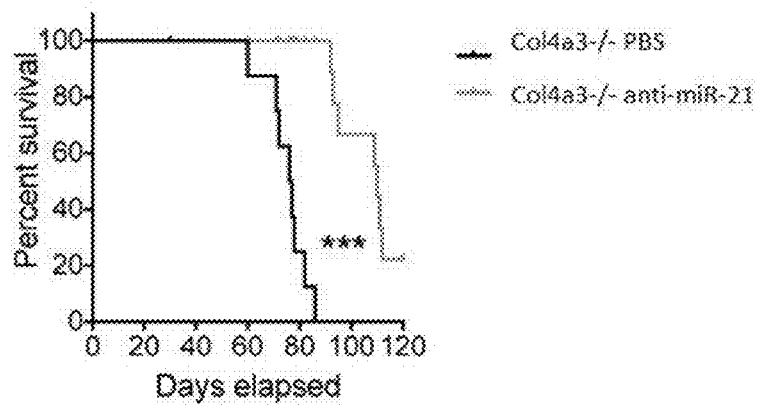

As expected, Col4a3−/− mice experienced weight loss beginning at around 9 weeks of age, and death occurred between 9 and 11 weeks of age. As shown in FIG. 8A, anti-miR-21 increased peak body weight and significantly delayed weight loss (p<0.01). As shown in FIG. 8B, anti-miR-21 significantly increased lifespan (p<0.001). Thus, treatment with anti-miR-21 not only delayed the weight loss, but importantly improved survival of Col4a3−/− mice.

Anti-miR-21Increases Survival in a Model of Alport Syndrome-dose Response Study

To evaluate the dose-responsive effects of anti-miR-21 on survival in an experimental model of Alport Syndrome, several doses of anti-miR-21 compound were administered to Col4a3−/− mice.

The structure of the anti-miR-21 compound is 5'-$A_E C_S ATC_S AGTC_S TGAU_S AAGC_S TA_E$-3' (SEQ ID NO: 3), where nucleosides not followed by a subscript indicate β-D-deoxyribonucleosides; nucleosides followed by a subscript "E" indicate 2'-MOE nucleosides; nucleosides followed by a subscript "S" indicate S-cEt nucleosides. Each internucleoside linkage is a phosphorothioate internucleoside linkage.

At 3 weeks of age, mice were genotyped to identify Col4a3−/− mice. Treatment groups were:

(1) Col4a3−/− mice, PBS administration once weekly, n=13;

(2) Col4a3−/− mice, 12.5 mg/kg anti-miR-21 administration, once weekly, n=12;

(3) Col4a3−/− mice, 25 mg/kg anti-miR-21 administration, once weekly, n=13;

(4) Col4a3−/− mice, 50 mg/kg anti-miR-21 administration, once weekly, n=12;
(5) Col4a3−/− mice, 25 mg/kg anti-miR-21 administration, twice weekly, n=12;

Treatments were administered starting on day 24. Animal weights were measured weekly, and lifespan was recorded. At week 7, blood was collected for measurement of BUN.

Figure 9A:
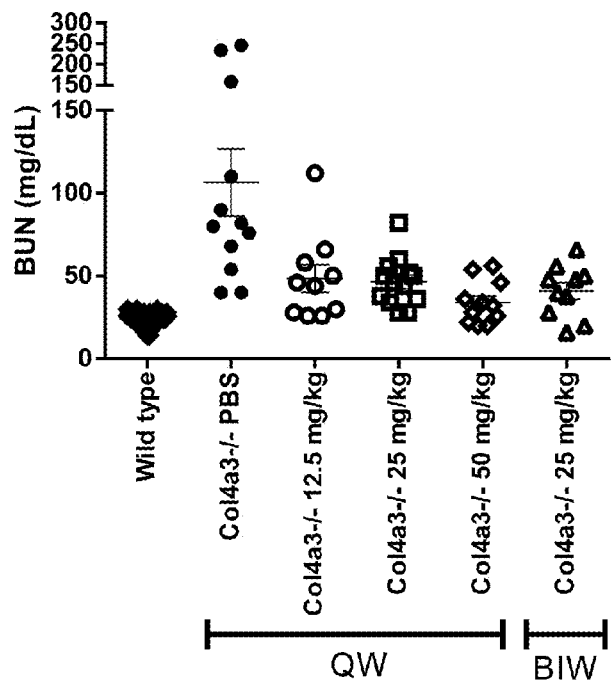
FIG. 9A-B. Anti-miR-21 improves kidney function and increases lifespan of Col4a3−/− mice in a dose-responsive manner (n=10-13 per treatment group). (A) Blood urea nitrogen at 7 weeks; (B) Lifespan of Col4a3−/− mice treated with anti-miR-21 at multiple doses, once weekly (QW) or twice weekly (BIW), or PBS control.

As shown in FIG. 9A, a reduction in BUN was observed in animals treated with anti-miR-21, relative to PBS-treated control animals. Although a reduction in BUN was observed, it was not strongly dose-responsive, perhaps due to the fact that the disease was more severe in the Col4a3−/− mice used for this experiment (the mice were obtained from a different vendor than the Col4a3−/− mice described in the previous examples). The observed reduction in BUN is an indicator of reduced kidney injury and damage and improved function.

Figure 9B:
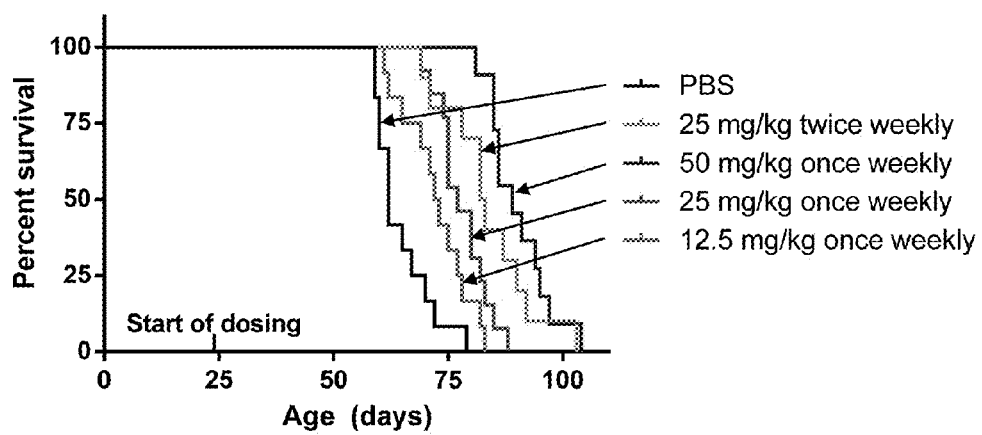

As shown in FIG. 9B, treatment with anti-miR-21 increased the lifespan of Col4a3−/− mice in a dose responsive manner. The increased lifespan was observed for both twice weekly and once weekly treatments. The median survival was as follows: PBS, 62 days; 12.5 mg/kg anti-miR-21 once weekly (QW), 72.5 days; 25 mg/kg anti-miR-21 once weekly (QW), 77 days; 50 mg/kg anti-miR-21 once weekly (QW), 89 days; 25 mg/kg anti-miR-21 twice weekly (BIW), 82.5 days.

Delay in the onset of kidney dysfunction and increased life expectancy in anti-miR-21 treated mice, relative to PBS-treated control mice, was observed, suggesting that anti-miR-21 is a therapeutic agent that can increase the life expectancy of subjects with Alport Syndrome.

Example 4

Anti-miR Distribution in the Kidney of Col4a3−/− Mice

Oligonucleotides, including anti-miR compounds, are known to distribute to several cell types within the kidney. As reported by Chau et al., *Sci Transl Med.*, 2012, 121ra18, following administration of a Cy3-labeled anti-miR to either normal mice or mice subjected to kidney injury (unilateral ureteral obstruction, a model of interstitial fibrosis), the greatest fluorescence intensity in the kidney was in proximal tubule epithelium. The endothelium, pericytes, myofibroblasts, and macrophages also all contained detectable amounts of Cy3-labeled anti-miR. However, the glomerulus, in particular podocytes, did not appear to take up significant amounts of anti-miR consistent with the known distribution of chemically modified oligonucleotides (Masarjian et al., *Oligonucleotides,* 2004, 14, 299-310).

To investigate the distribution of anti-miR in a mouse model of Alport Syndrome, Cy3-labeled anti-miR compound was administered to two different groups of Col4a3−/− mice, one at 6 weeks of age (n=3) and one at 8 weeks of age (n=4) and to one group of wild type mice at 8 weeks of age (n=3). Two days following administration of the anti-miR compound, animals were sacrificed and kidneys were harvested and processed for histological analysis.

Sections of kidney tissue were co-labeled with antibodies specific to several different cellular markers to identify anti-miR uptake in particular cell types Staining was performed for alpha-SMA (a myofibroblast marker), PDGFR-beta (a pericyte/myofibroblast marker), CD31 (an endothelial cell marker), F4/80 (a macrophage marker), and GP38 (a podocyte marker). As expected, anti-miR compound was taken up into the proximal tubule epithelium, pericytes, myofibroblasts, and macrophages. In contrast to previous observations in normal mice and mice with interstitial fibrosis, in the Col4a3−/− mice anti-miR was taken up into the glomerulus, including into podocytes.

As described herein, the efficacy observed following anti-miR-21 administration in an experimental model of Alport Syndrome is accompanied by improvements not only in interstitial fibrosis surrounding tubules but also fibrosis in the glomeruli (known as glomerulosclerosis). These data suggest that those improvements may be directly related to anti-miR-21 effects in the glomeruli, in addition to or instead of feedback from an improved tubule structure and function.

What is claimed is:

1. A method of treating Alport Syndrome comprising administering to a subject having or suspected of having Alport Syndrome a modified oligonucleotide consisting of 15 to 22 linked nucleosides, wherein the nucleobase sequence of the modified oligonucleotide is at least 90% complementary to miR-21, wherein the subject is male and wherein the Alport syndrome is the X-linked form of Alport syndrome.

2. The method of claim 1, wherein the nucleobase sequence of the modified oligonucleotide is at least 95% complementary to the nucleobase sequence of miR-21 (SEQ ID NO: 1).

3. The method of claim 1, wherein the modified oligonucleotide comprises at least one modified nucleoside.

4. The method of claim 3, wherein the at least one modified nucleoside is selected from an S-cEt nucleoside, a 2'—O-methoxyethyl nucleoside, and an LNA nucleoside.

5. The method of claim 1, wherein the modified oligonucleotide comprises at least one modified internucleoside linkage.

6. The method of claim 1, wherein each internucleoside linkage of the modified oligonucleotide is a modified internucleoside linkage.

7. The method of claim 5, wherein the modified internucleoside linkage is a phosphorothioate internucleoside linkage.

8. The method of claim 6, wherein the modified internucleoside linkage is a phosphorothioate internucleoside linkage.

9. The method of claim 1, wherein the nucleobase sequence of the modified oligonucleotide is 100% complementary to the nucleobase sequence of miR-21.

10. The method of claim 1, wherein the modified oligonucleotide consists of 19 linked nucleosides.

11. The method of claim 1, wherein the modified oligonucleotide comprises S-cEt nucleotides, 2'—O-methoxyethyl nucleosides, and β-D-deoxyribonucleosides.

* * * * *